US011707581B1

(12) United States Patent
Nachshon et al.

(10) Patent No.: US 11,707,581 B1
(45) Date of Patent: Jul. 25, 2023

(54) INFUSION DEVICE

(71) Applicant: Quality in Flow LTD, Petach Tikva (IL)

(72) Inventors: Dov Nachshon, Rosh HaAyin (IL); David Nassi, Sdei Hemed (IL)

(73) Assignee: Quality in Flow LTD, Petach Tikva (IL)

( * ) Notice: Subject to any disclaimer, the term of this patent is extended or adjusted under 35 U.S.C. 154(b) by 0 days.

(21) Appl. No.: 17/694,881

(22) Filed: Mar. 15, 2022

(51) Int. Cl.
*A61M 5/44* (2006.01)
*A61M 39/10* (2006.01)

(52) U.S. Cl.
CPC .............. *A61M 5/445* (2013.01); *A61M 5/44* (2013.01); *A61M 2039/1022* (2013.01); *A61M 2205/0233* (2013.01); *A61M 2205/3313* (2013.01); *A61M 2205/3379* (2013.01); *A61M 2205/3653* (2013.01)

(58) Field of Classification Search
CPC .................................. A61M 5/44; A61M 5/445
See application file for complete search history.

(56) References Cited

U.S. PATENT DOCUMENTS

| | | | |
|---|---|---|---|
| 2008/0228142 A1* | 9/2008 | Elazari-Volcani | A61M 5/44 604/114 |
| 2015/0265767 A1 | 9/2015 | Vazquez et al. | |
| 2015/0342463 A1* | 12/2015 | Garibotto | A61B 5/0086 600/474 |
| 2019/0030261 A1* | 1/2019 | Norman | A61M 5/44 |
| 2019/0381230 A1* | 12/2019 | Biewer | A61M 1/28 |

OTHER PUBLICATIONS

QinFLOW "Compact Disposable Unit (CDU) (QPORT0500): Sterile (Per-Patient) Warming Component, Compatible With All Wamor Configurations, i.e. the Warrior Lite, Warrior, Warrior EXTREME, Warrior AC, and Warrior Hybrid (Note: the CDU Must Be Used Together With a Warrior Configuration!)", QinFLOW, Version 1, 2 P., Apr. 2020.
QinFLOW "Warrior Lite (Extra Power Batterv (Q1310S0000): High Performance Yet Compact and Light Blood and IV Fluid Warmer for Space and Weight Constrained Rescue Gears, First Responders, and Critical Care Transports", QinFLOW, Version 6, 2 P., Jun. 2020.
International Search Report and the Written Opinion dated Jun. 1, 2023 From the International Searching Authority Re. Application No. PCT/IL2023/050273 (8 Pages).

* cited by examiner

*Primary Examiner* — Jenna Zhang

(57) ABSTRACT

A device for preparation of infusion fluid including: a first portion including: a fluid conduit comprising electrically conductive material; electrical circuitry electrically connected to the fluid conduit; a second portion selectively couplable to the first portion and including: at least one sensor for sensing fluid within the fluid conduit; a power supply and/or connectivity to a power supply; wherein mechanical coupling of the first portion to the second portion electrically connects the electrical circuitry to the power supply and/or connectivity to the power supply.

27 Claims, 10 Drawing Sheets

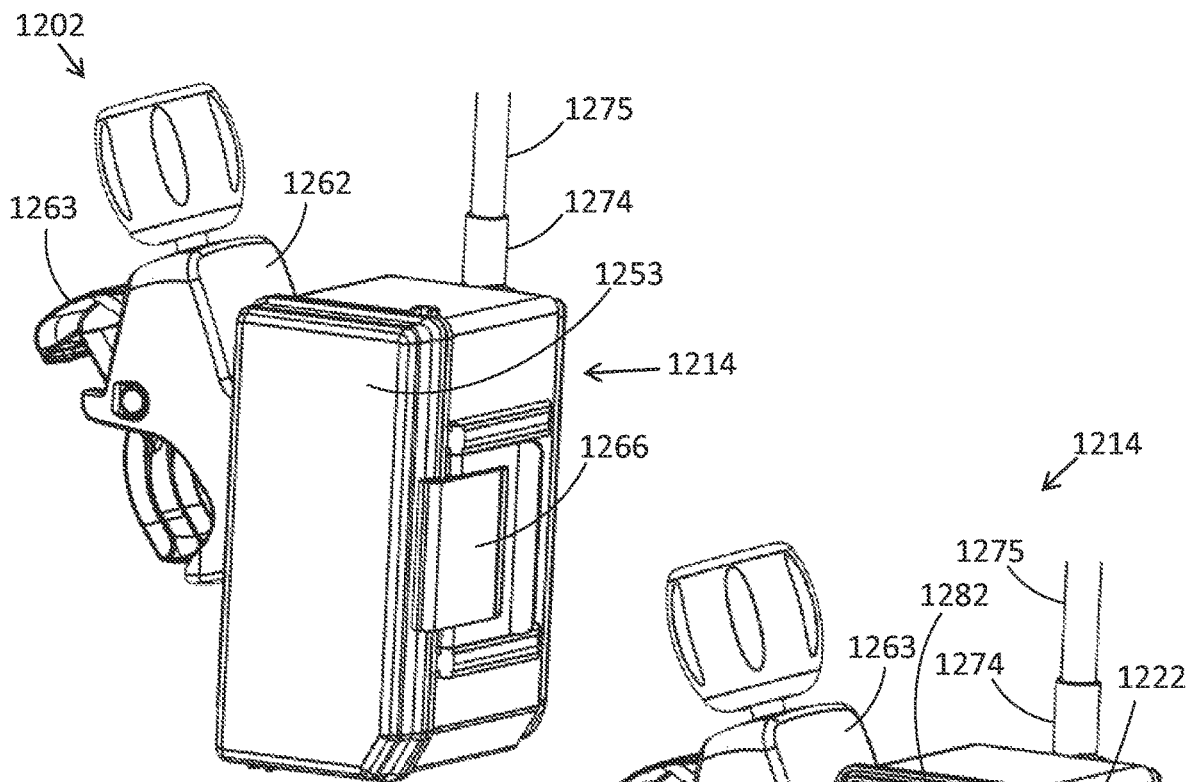
FIG. 12A
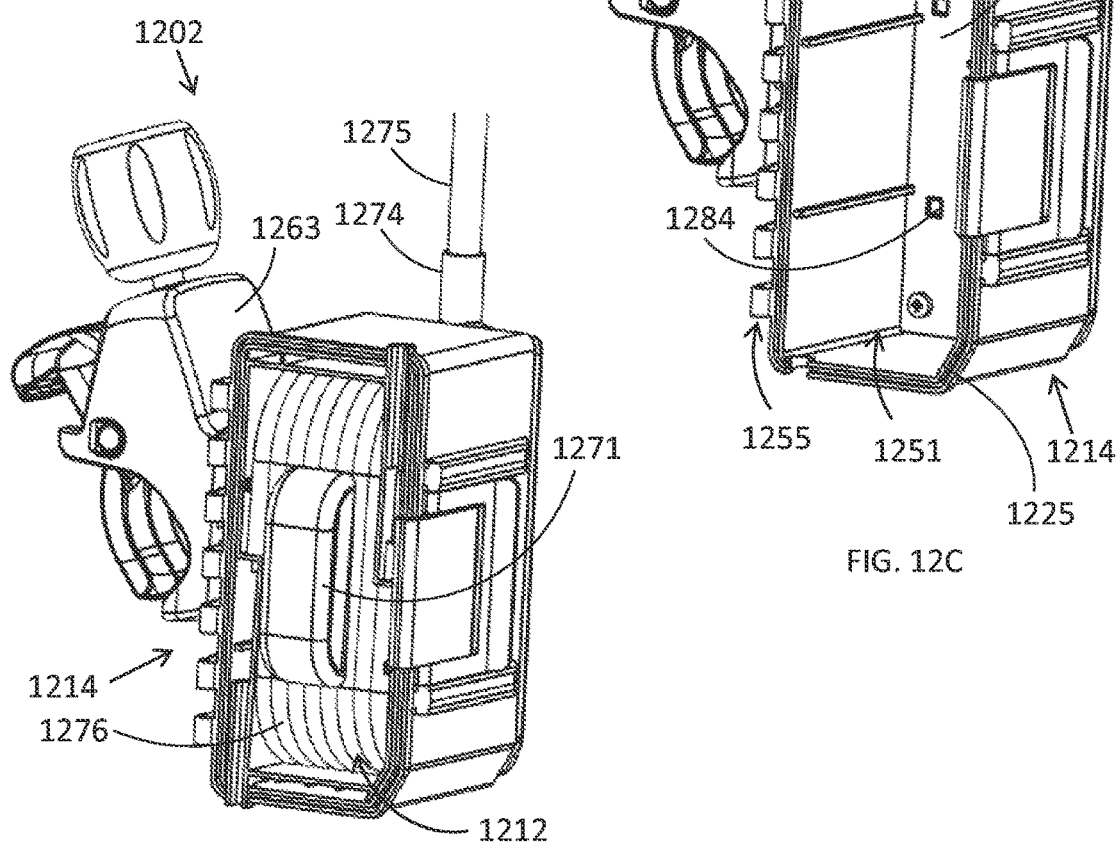
FIG. 12B
FIG. 12C

INFUSION DEVICE

FIELD AND BACKGROUND OF THE INVENTION

The present invention, in some embodiments thereof, relates to an infusion system and, more particularly, but not exclusively, to an infusion device for infusing warmed fluid to a subject.

Background art includes U.S. Pat. Nos. 9,533,109, 10,485,921, 10,747,241, and 4,657,160.

SUMMARY OF THE INVENTION

Following is a non-exclusive list including some examples of embodiments of the invention. The invention also includes embodiments which include fewer than all the features in an example and embodiments using features from multiple examples, also if not expressly listed below.

Example 1. A device for preparation of infusion fluid comprising:
a first portion comprising:
a fluid conduit comprising electrically conductive material;
electrical circuitry electrically connected to said fluid conduit;
a second portion selectively couplable to the first portion and comprising:
at least one sensor for sensing fluid within said fluid conduit;
a power supply and/or connectivity to a power supply;
wherein mechanical coupling of said first portion to said second portion electrically connects said electrical circuitry to said power supply and/or connectivity to said power supply.

Example 2. The device according to example 1, wherein said fluid conduit is elongated, having a shape including one or more change in direction and following a path around an internal volume.

Example 3. The device according to example 2, wherein said fluid conduit is a coil of tubing, said fluid conduit coiling around said internal volume.

Example 4. The device according to any one of examples 2-3, wherein said second portion includes a body sized and shaped to fit into said internal volume and wherein said mechanical coupling comprises inserting said body into said internal volume.

Example 5. The device according to example 4, wherein said body fits into said internal volume through an opening to said internal volume and wherein said second portion includes a base portion larger than said opening.

Example 6. The device according to any one of examples 1-5, wherein said first portion is sized and shaped to fit into a lumen of said second portion.

Example 7. The device according to example 6, wherein said lumen of said second portion comprises a cover, which is closed to hold said first portion in position within said lumen of said second portion.

Example 8. The device according to any one of examples 1-7, wherein said second portion comprises at least one second portion electrical contact;
wherein said electrical circuitry of said first portion comprises at least one first portion electrical contact where, when mechanically coupled said at least one second portion electrical contact contacts said second portion electrical contact.

Example 9. The device according to any one of examples 1-8, wherein said at least one sensor comprises a non-contact sensor.

Example 10. The device according to example 9, wherein said non-contact sensor is an infrared (IR) sensor.

Example 11. The device according to any one of examples 1-10, wherein said second portion comprises a housing, were said at least one sensor is disposed within said second portion housing, wherein upon connecting of said first portion to said second portion said at least one sensor is positioned, adjacent to a portion of said conduit.

Example 12. The device according to example 11, wherein said housing encloses circuitry of said second portion.

Example 13. The device according to any one of examples 11-12, wherein said sensor senses said conduit through a window in said second portion housing.

Example 14. The device according to example 13, wherein said window comprises material transparent to IR radiation.

Example 15. The device according to examples 13-14, wherein said window comprises germanium.

Example 16. The device according to any one of examples 1-15, wherein said first portion comprises a housing which extends around said conduit while having one or more openings to the conduit, where, when said first portion and said second portion are coupled said one or more sensor is adjacent to said one or more openings.

Example 17. The device according to any one of examples 1-16, wherein said at least one sensor comprises a contact sensor, where said contact sensor makes contact with said conduit for sensing thereof, upon coupling of said first portion and said second portion.

Example 18. The device according to any one of examples 1-17, wherein said electrical power supplied by said power supply to said fluid conduit through electrical circuitry acts to heat said conduit.

Example 19. The device according to any one of examples 1-18, comprising a processor configured to:
receive a measurement signal from said at least one sensor; and
generate control signals to control said power supply, based on said measurement signal.

Example 20. The device according to any one of examples 8-19, wherein said first portion comprises at least one electrical connector electrically connecting said conduit to said first portion electrical contact.

Example 21. The device according to any one of examples 1-20, wherein said electrical connector comprises a portion configured to be slid onto said conduit.

Example 22. The device according to example 21, wherein said portion is an electrical contact between said connector and said conduit.

Example 23. The device according to any one of examples 21-22, wherein said portion comprises a lumen sized and shaped to receive said conduit and form electrical contact with said conduit.

Example 24. The device according to any one of examples 21-23, wherein said portion is a loop which extending around at least 50% of a circumference of said conduit.

Example 25. The device according to any one of examples 1-24, wherein said second portion comprises at least one electrical contact housed in a removable portion of said second portion.

Example 26. The device according to any one of examples 1-25, comprising a microswitch activated by coupling of said first portion and said second portion.

Example 27. The device according to example 26, wherein activating of said microswitch enables power transfer from said power supply to said electrical circuitry.

Example 28. The device according to any one of examples 26-27, wherein said microswitch is housed within a removable portion of said second portion with electrical contacts of said second portion.

Example 29. The device according to any one of examples 1-28, wherein one or more portion of said conduit is covered with an infrared absorptive material.

Example 30. The device according to any one of examples 1-29, wherein said power supply is external to said device and connected to said second portion via electrical circuitry.

Example 31. A method of infusion fluid preparation comprising:

mechanically coupling and electrically connecting a fluid conduit comprising electrically conductive material to a power supply, current provided by said power supply heating said fluid conduit;

supplying infusion fluid to an inlet of said fluid conduit;

sensing said fluid conduit using one or more non-contact sensor separated from said fluid conduit to provide a measurement signal; and controlling said power supply, based on said measurement signal.

Example 32. The method according to example 31, wherein said sensing comprises sensing of infrared light.

Example 33. The method according to any one of examples 31-32, wherein said one or more non-contact sensor is located within a housing, where said conduit is outside of said housing.

Example 34. The method according to example 33, wherein said power supply or connectivity to said power supply is located within said housing.

Example 35. A base of an infusion device comprising:

a housing having a window;

a sensor configured to sense a fluid conduit outside said housing through said window; and a power supply or connectivity to a power supply.

Example 36. The base according to example 17, comprising a processor or connectivity to a processor configured to:

receive measurements from said sensor; and control said power supply, based on said measurements.

Example 37. The base according to any one of examples 15-16, wherein said sensor is an infrared light sensor.

Example 38. A device for preparation of infusion fluid comprising:

a fluid conduit comprising electrically conductive material;

a first electrical connector attached to a first portion of said fluid conduit;

a second electrical connector attached to a second portion of said fluid conduit, said fluid conduit forming an electrically conductive path between said first portion and said second portion;

one or both of said connectors comprising:

a loop sized and shaped to extend around and contact a portion of said infusion conduit;

a first contact extending from a first side of said loop; and a second contact extending from a second side of said loop.

Example 39. The device according to example 38, wherein one or both of said first contact and said second contact are sized and/or shaped to be deflected by a contact electrically connected to a power supply.

Example 40. The device according to any one of examples 38-39, comprising an housing which covers an outer surface of said conduit, while leaving an inner surface open to an internal volume.

Example 41. The device according to example 40, wherein said conduit has a coil shape including at least two turns and coils around said internal volume.

Example 42. The device according to example 41, comprising a second portion selectively couplable to the first portion and comprising:

said power supply and/or connectivity to said power supply;

said contact electrically connected to said power supply; and at least one sensor for sensing fluid within said fluid conduit.

Example 43. An electrical connector for connection of an infusion conduit to a power supply comprising:

a loop sized and shaped to extend around and contact a portion of a tubular infusion conduit;

a first contact extending from a first side of said loop; and a second contact extending from a second side of said loop.

Example 44. A device for preparation of infusion fluid comprising:

a first portion comprising:

a fluid conduit through which fluid to be infused is passed;

a second portion selectively couplable to the first portion and comprising:

at least one sensor for sensing fluid within said fluid conduit;

wherein mechanical coupling of said first portion to said second portion positions said at least one sensor in proximity to said fluid conduit for measuring said fluid conduit. Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such inspecting objects, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 12A is a simplified schematic of an infusion device, according to some embodiments of the invention;

FIG. 12B is a simplified schematic of an infusion device, according to some embodiments of the invention; and FIG. 12C is a simplified schematic of an second portion of an infusion device, according to some embodiments of the invention.

DESCRIPTION OF SPECIFIC EMBODIMENTS OF THE INVENTION

Figure 1:
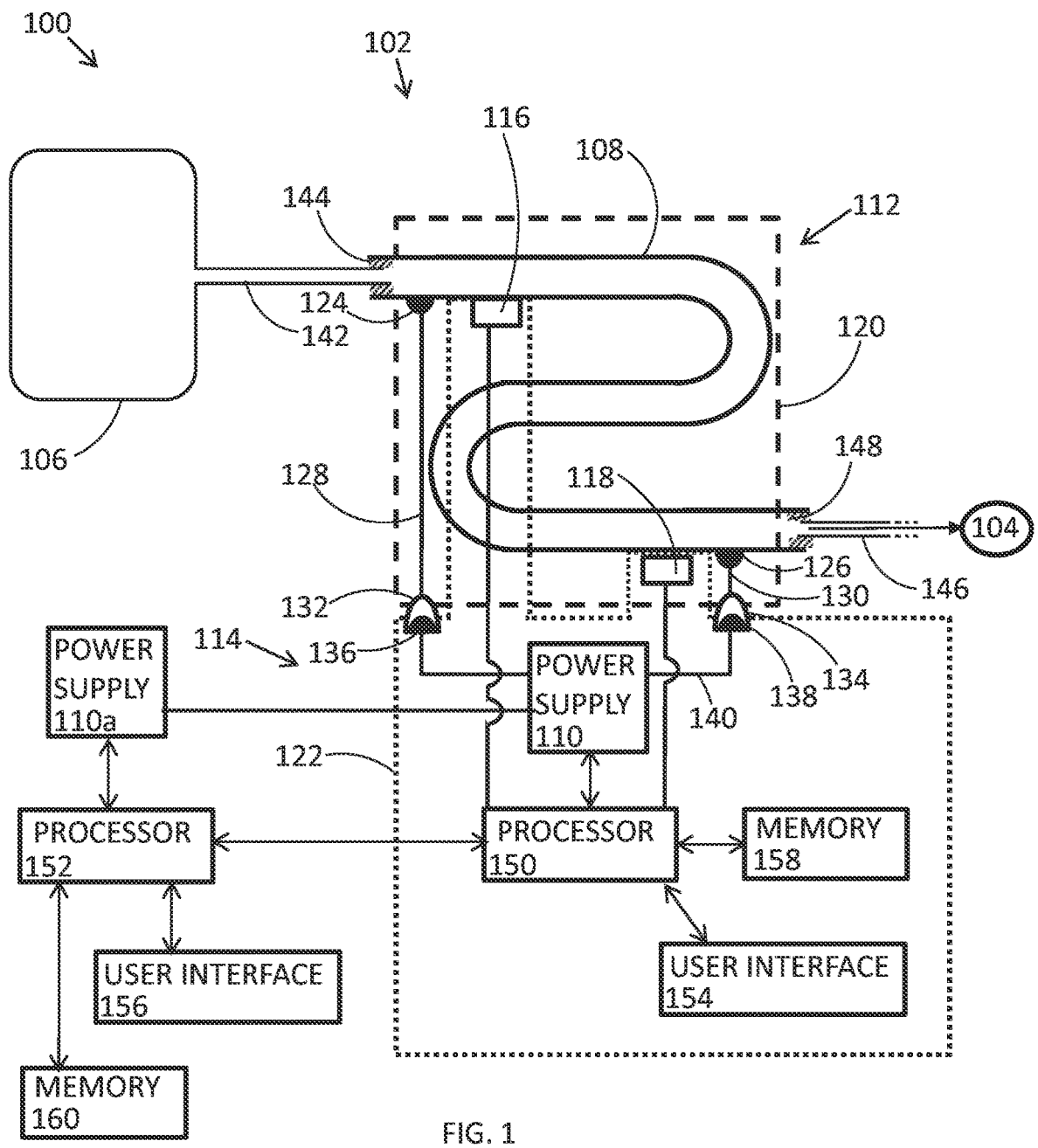
FIG. 1 is a simplified schematic of a system, according to some embodiments of the invention.

The present invention, in some embodiments thereof, relates to an infusion system and, more particularly, but not exclusively, to an infusion device for infusing warmed fluid to a subject.

Overview

A broad aspect of some embodiments of the invention relates to preparation of infusion fluid, where a conduit through which infusion fluid flows to prepare the fluid for infusion is disposable, and where circuitry for preparation (e.g. heating) of the infusion fluid, for example, including sensors and/or sensor circuitry is hosted by a separate, re-usable portion which is selectively attachable to the conduit (e.g. to a portion hosting the conduit).

An aspect of some embodiments of the invention relates to an infusion device including a first portion (e.g. lacking sensor/s) hosting a conduit for infusion fluid and a second portion hosting one or more sensor for measuring parameter/s of the infusion fluid. Optionally, in some embodiments, the second portion hosts a power supply and/or connectivity to a power supply for supply of electrical power where, in some embodiments, mechanical coupling of the portions electrically connects the power supply to the first portion, for treatment of infusion fluid.

In some embodiments, fluid treatment and/or preparation includes temperature control (e.g. heating and/or cooling and/or maintaining the fluid at a desired temperature and/or temperature range) of the fluid and/or a conduit through which the fluid flows. Where, in some embodiments, the fluid is heated, for example, by heating of one or more portion of the conduit. In some embodiments, the conduit includes conductive material and current passing through the conduit (and supplied by the power supply) heats the conduit and/or infusion fluid therewithin.

In an exemplary embodiment, the fluid temperature is controlled to be within a range around normal human body temperature (37 degrees centigrade), for example, 36-39 degrees Centigrade, or within 30%, or 20%, or 10%, or 5% or lower or higher or intermediate percentages of body temperature. In some embodiments, control allows temperatures to fall to below body temperature by a larger proportion than above body temperature, for example, maintained to between 35-37 degrees Centigrade.

In some embodiments, the fluid temperature is controlled as part of treatment of a condition. For example, in some embodiments, fluid temperature is controlled to be above normal human body temperature, for example, to treat hypothermia. For example, controlled to be between 37-42 degrees Centigrade, or 38-42 degrees Centigrade, or 40-42 degrees Centigrade, or about 42 degrees Centigrade, or lower or higher or intermediate temperatures or ranges. For example, in some embodiments, fluid temperature is controlled to be below normal human body temperature, for example, as part of treatment for one or more of; head injury, oxygen deprivation, fever. For example, controlled to be between 30-36 degrees Centigrade, or 32-34 degrees Centigrade, or about 33 degrees Centigrade, or lower or higher or intermediate temperatures or ranges.

In some embodiments, measured body temperature of the subject is used as feedback to control of temperature of the fluid. Where, for example, the processor generating control signals receives measurement/s from one or more sensor collecting body temperature measurement/s of the patient.

Alternatively or additionally, in some embodiments, measurement/s of air temperature of the surroundings (e.g. as supplied to the processor generating control signals by one or more sensor e.g. positioned externally on one or more of the device portion/s e.g. an external sensor providing data to the processor) of the patient is used as a feedback to control of temperature of the fluid.

In some embodiments, fluid is treated and/or prepared alternatively or additionally to temperature control. For example, one or more of filtered, electrically charged, agitated, flow rate is controlled.

In some embodiments, infusion fluid includes one or more of blood, blood product/s, medication, hydration fluid.

Although, in this document, description is generally with referent to supply of infusion fluid other fluid supplies to a patient are envisioned and/or encompassed. For example: In some embodiments, supply and/or preparation (e.g. heating) of fluid is for irrigation fluid e.g. during a medical procedure e.g. during surgery. In some embodiments, supply and/or preparation is of fluid for tube feeding and/or hydration, for example, through one or more of a tasogastric tube, a nasojejunal tube, a percutaneous endoscopic gastrostomy, and a jejunostomy tube.

An aspect of some embodiments of the invention relates to attaching the first portion and the second portion to accurately align and/or maintain alignment of sensors of the second portion with the conduit of the first portion.

In some embodiments, the attachment includes locking the portions together, once they are connected.

In some embodiments, mechanical connection of the two portions closes a switch. Where, in some embodiments, power is supplied to circuitry of the portion/s only when the switch is closed.

In some embodiments, housing of the first and/or second portions, maintains the conduit and/or sensors in a fixed spatial relationship with each other.

An broad aspect of some embodiments of the invention relates to an easily constructed and/or inexpensive first portion. In some embodiments, the first portion includes a conduit, and a housing for the conduit where the housing holds the conduit in position. In some embodiments, the first portion includes connectors for connection of the conduit to a power supply. In some embodiments, a first portion with a small number of parts (e.g. housing, conduit, and optionally connectors) is easily constructed and/or cleaned and/or tested. A potential benefit of reduced circuitry e.g. no sensors is lack of requirement, in some embodiments, of electrical testing e.g. safety testing.

In some embodiments, the first portion includes a housing which has at most 2 portions, or at most 1-4 portions, or lower or higher or intermediate numbers of portions. In some embodiments, the housing does not enclose the conduit, allowing portion/s of the conduit (e.g. inner portions of the conduit adjacent to an inner space delineated by the shape of the conduit) to be in close contact with other portion/s of the device e.g. sensor/s of the second portion.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary System

FIG. 1 is a simplified schematic of a system 100, according to some embodiments of the invention.

In some embodiments, system 100 includes an infusion device 102 which prepares fluid for infusion into a subject 104. In some embodiments, fluid is received from a fluid reservoir 106, passing through infusion device 102, where the fluid is treated and/or prepared for infusion before being delivered to subject 104.

In some embodiments, infusion device 102 includes a fluid conduit 108 through which fluid to be prepared for infusion flows.

In some embodiments, fluid passing through fluid conduit 108 is heated by heating of the fluid conduit 108 itself. In some embodiments, fluid conduit 108 includes conductive material and heating of conduit 108 is by passing an electrical current through material of conduit 108.

In some embodiments, system 100 includes one or more power supply 110, 110a which supply current to conduit 108 for heating of conduit 108.

In some embodiments, infusion device 102 itself includes a power supply 110. For example, in some embodiments, second portion 114 includes a power supply. Alternatively or additionally, to including power supply 110, in some embodiments, infusion device 102 includes connectivity to an external power supply 110a. In an exemplary embodiment, infusion device 102 itself does not include a power supply, but includes connectivity to an external power supply 110a.

In some embodiments, infusion device 102 includes at least two connectable portions 112, 114, a first portion 112 including conduit 108, and a second portion 114 including power supply 110. In some embodiments, connection of the two portions 112, 114, connects power supply 110 (and/or connectivity to a power supply) to conduit 108 for heating of the conduit 108.

In some embodiments first portion 112 includes a housing 120. In some embodiments, second portion 114 includes a housing 122. Where, in some embodiments, portions 112, 114 are connected by connection of their housings 120, 122 e.g. by one or more housing connector (e.g. housing connector 466 FIG. 4A, FIG. 5). In some embodiments, housing connector/s prevent relative movement between sensors and conduit 108, potentially increasing accuracy of measurement of conduit 108 by the sensors.

In some embodiments, first portion 112 is single use (and/or configured to be sterilized), and in some embodiments, second portion 114 is multi-use, for example, does not contact infusion fluids.

In some embodiments, first portion 112 includes electrical circuitry 124, 126, 128, 130, 132, 134 electrically connecting conduit 108 to power supply 110 e.g. via electrical circuitry 136, 138, 140 of second portion 114.

In some embodiments, first portion conduit contacts 126, 128 connect conduit 108 to first portion connector contacts 132, 134 e.g. by first portion connectors 128, 130.

In some embodiments, first portion contacts 132, 134 connect to second portion contacts 136, 138. Where, in some embodiments, first portion contacts 132, 134 electrically (and optionally, mechanically) connect to second portion contacts 136, 138.

Optionally, in some embodiments, second portion 114 includes one or more sensor 116, 118. In some embodiments, sensor/s 116, 118 measure one or more feature of conduit 108, for example conduit temperature, for one or more portion of conduit 108.

In some embodiments, sensors 116, 118 include one or more contact and/or non-contact sensor. Where contact sensors contact a portion of the device to be measured e.g. conduit 108. In some embodiments, sensors 116, 118 include one or more temperature sensor e.g. IR sensor e.g. thermistor.

In some embodiments, connecting of first portion 112 and second portion 114 brings contact sensor/s into contact with portion/s to be measured. For example, in some embodiments, a contact sensor of second portion 114 is brought into close enough contact with conduit 108 (e.g. by sizing and/or shaping and/or elastic and/or plastic deformation of one or more portion) for the sensor to measure conduit 108. For example, in some embodiments, contact sensor/s are spring biased to contact portion/s to be measured. For example, in some embodiments, after and/or as part of connecting of portions 112, 114, contact sensor/s are moved into contact with portion/s to be measured.

Figure 4A:
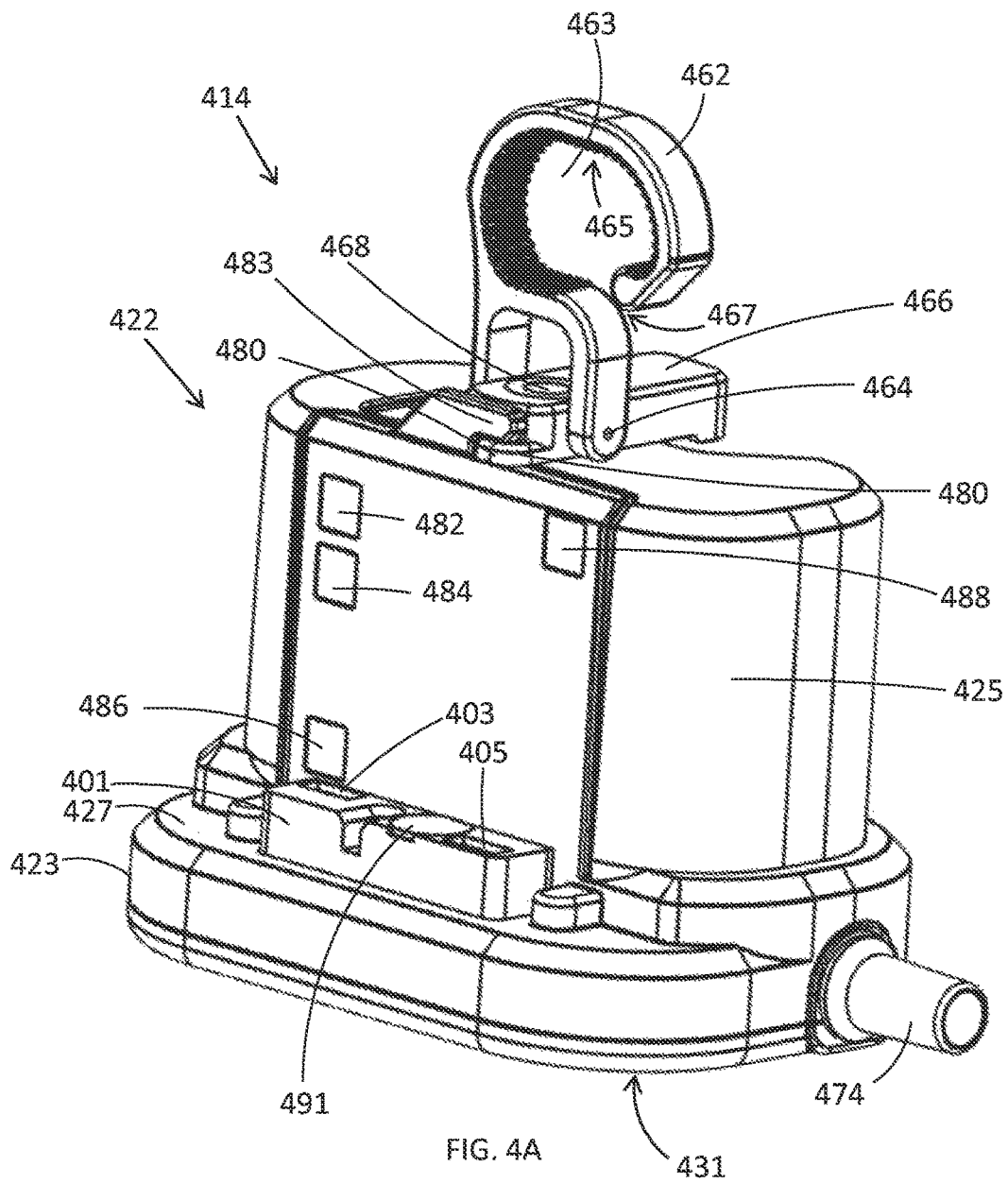
FIG. 4A is a simplified schematic of a second portion of an infusion device, according to some embodiments of the invention.

In an exemplary embodiment, sensor/s 116, 118 include non-contact sensor/s e.g. infrared (IR) sensor/s (and/or which sense temperature of conduit 108 through housing 112 (e.g. through hole/s and/or transparent window/s in housing 112 e.g. windows 482, 484, 486, 488, 490 FIG. 4A).

In some embodiments, conduit 108 includes material which is non IR-reflective. A potential advantage being increased accuracy of measurement of temperature of the conduit by IR sensors. In an exemplary embodiment, at least portion/s of the conduit adjacent to IR sensors include (e.g. are coated and/or covered) e.g. with IR absorptive material e.g. coated in a non-glossy (e.g. matt) and/or black colored material. In some embodiments, the coating is thin (e.g. less than 0.5 mm thick, or less than 0.1 mm thick, or lower or higher or intermediate thicknesses a potential benefit being reduced insulation of the conduit by the coating and/or potentially increased accuracy of temperature measurement).

In some embodiments, the non-reflective material is located only on region/s of the conduit being sensed, for example, where patch/es of the conduit include the material. For example, where, in some embodiments, non-reflective material is adhered to portion/s of the conduit e.g. sticker/s are applied.

Optionally, in some embodiments, device 102 includes additional or alternative sensor/s to temperature sensor/s. For example, a flow rate sensor to sense flow within conduit 108. For example, an ultrasound sensor to sense flow rate within conduit through one or more ultrasound transparent (e.g. with low enough attenuation) portion of conduit 108. Where the ultrasound sensor, in some embodiments, is hosted by the second portion e.g. measuring conduit 108 through one or more window or hole in the second portion housing.

In some embodiments, flow rate of fluid and/or a volume of fluid supplied (e.g. in a given time) is determined using supplied power to the conduit, over time.

Where, in some embodiments, processor/s 150, 152, record power supplied by power supply/s 110, 110a e.g. over time. In some embodiments, measured temperature of one or more portion of the conduit (e.g. as measured by one or more of sensors 116, 118.

In some embodiments, flow rate is determined using equation 1 below:

$$Q = m\ C\ Z\Delta T \qquad \text{equation 1}$$

Where Q is the heat energy supplied, m is the mass of fluid, C is the specific heat capacity of the material being heated, and $\Delta T$ is the change in temperature in the material being heated.

Where, in some embodiments, $\Delta T$ is determined using measurement/s (e.g. sensor measurement/s 116, 118 of the conduit at one or more portion of the conduit) and/or an assumption (e.g. regarding input and/or output fluid temperature).

Where, in some embodiments, if Q (e.g. via power supplied), C (e.g. about 4 for blood where, in some embodiments, specific heat capacity of the material of the conduit and/or responsiveness of the material of the conduit to power changes, are taken into account), and $\Delta T$ (e.g. measured using sensor/s of the device) are known then the mass per time period (e.g. determined using density of the fluid), in some embodiments, is used to determine flow rate of the fluid and/or a volume supplied in a given amount of time.

A potential benefit of being able to determine volume supplied is increased information to a caregiver regarding a quantity of fluid delivered. Where, in some embodiments, user interface/s 154, 156 are used to display fluid flow and/or total volume infused for a time period. Where, in some embodiments, a user specifies (e.g. selects at a user interface) which portion/s of the data to be displayed, for example, flow rate and/or volume, and optionally for a specified (e.g. selected at a user interface) time period.

In some embodiments, fluid reservoir 106 connects to conduit 108 via an input fluid connector 144 which, in some embodiments, is an air sealed connection. In some embodiments, fluid reservoir 106 connects to connector 144 via tubing 142.

In some embodiments, an infusion apparatus 146 (e.g. transferring fluid to subject 104) is connected to conduit via an output fluid connector 148 which, in some embodiments, is an air sealed connection.

In some embodiments, system 100 includes one or more processor 150, 152. Where, in some embodiments, processor 150 receives sensor measurement signals from sensors/116, 118.

In some embodiments, processor/s 150, 152, sends control signals to power supply 110 to control flow of current from power supply 110 to conduit 108, for example, based on the sensor measurements. In some embodiments, system 100 includes a device processor 150 hosted by second portion 114.

In some embodiments, sensor/s 116, 118, are digital sensors, providing a digital output. In some embodiments, this digital measurement signal is converted to an analog signal e.g. by processor 150, 152.

Alternatively or additionally to having a device processor 150, in some embodiments, system includes an external processor 152 e.g. hosted by an external electrical device/s and/or the cloud. For example, in some embodiments, device 102 itself does not include a processor and processing is provided by an external processor 152.

FIG. 1 illustrates processor 152 connected (wired and/or wireless connection) with device processor 150. However, in some embodiments, processor 152 directly interfaces with other portion/s of infusion device 102 e.g. power supply 110.

In some embodiments, system 100 includes one or more user interface 154, 156. For example, one or more device user interface 154 e.g. hosted by second portion 114. For example, one or more external user interface 156 e.g. hosted by an external electronic device. In some embodiments, a user inputs control command/s and/or receives communication/s (e.g. measurement data and/or alert/s) through user interface/s 156, 154.

In some embodiments, system 100 includes one or more memory 158, 160. For example, a device memory 158 e.g. hosted by second portion 114. For example, one or more external memory 160 e.g. hosted by an external electronic device.

In an exemplary embodiment, second portion 114 hosts sensors 116, 118 but lacks a processor and/or power supply, hosting connectivity to power supply 110a and/or processor 152. In some embodiments, an additional portion, a third portion, hosts power supply 110a and processor 152.

Exemplary Method

Figure 2:
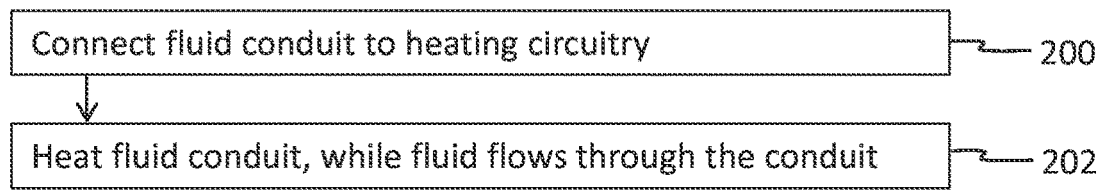
FIG. 2 is a method of infusion fluid preparation, according to some embodiments of the invention.

FIG. 2 is a method of infusion fluid preparation, according to some embodiments of the invention.

At 200, in some embodiments, a fluid conduit is connected to heating circuitry. For example, referring to FIG. 1, first portion 112 is connected to second portion 114.

At 202, in some embodiments, temperature of the fluid flowing through the fluid conduit and/or the fluid conduit temperature is controlled while fluid flows through the conduit.

In some embodiments, a temperature of the fluid conduit and/or infusion fluid is controlled using feedback measurements of sensor/s sensing the conduit and/or fluid (e.g. sensor/s 116, 118 FIG. 1).

In some embodiments, based on sensed temperature power supplied to the conduit is controlled.

In some embodiments, a value of current supplied to the conduit is controlled, based on the sensed temperature. For example, where current is supplied to the conduit in pluses, the current supplied is adjusted, based on the sensed measurements (e.g. the duty cycle of the pulses remains the same but the magnitude is adjusted).

In some embodiments, pulse width modulation (PWM) is employed in temperature regulation control, for example, a duty cycle is adjusted, based on the sensed measurements (e.g. the magnitude of pulses remains the same, but the duty cycle is adjusted).

In some embodiments, both pulse width and magnitude are adjusted.

In some embodiments, one or more other method e.g. in the field of temperature control is employed, for example, for control of the power supplied for heating of the conduit, based on sensed temperature of the conduit (and/or fluid there within).

Exemplary Multi-Portion Infusion Device

Figure 3A:
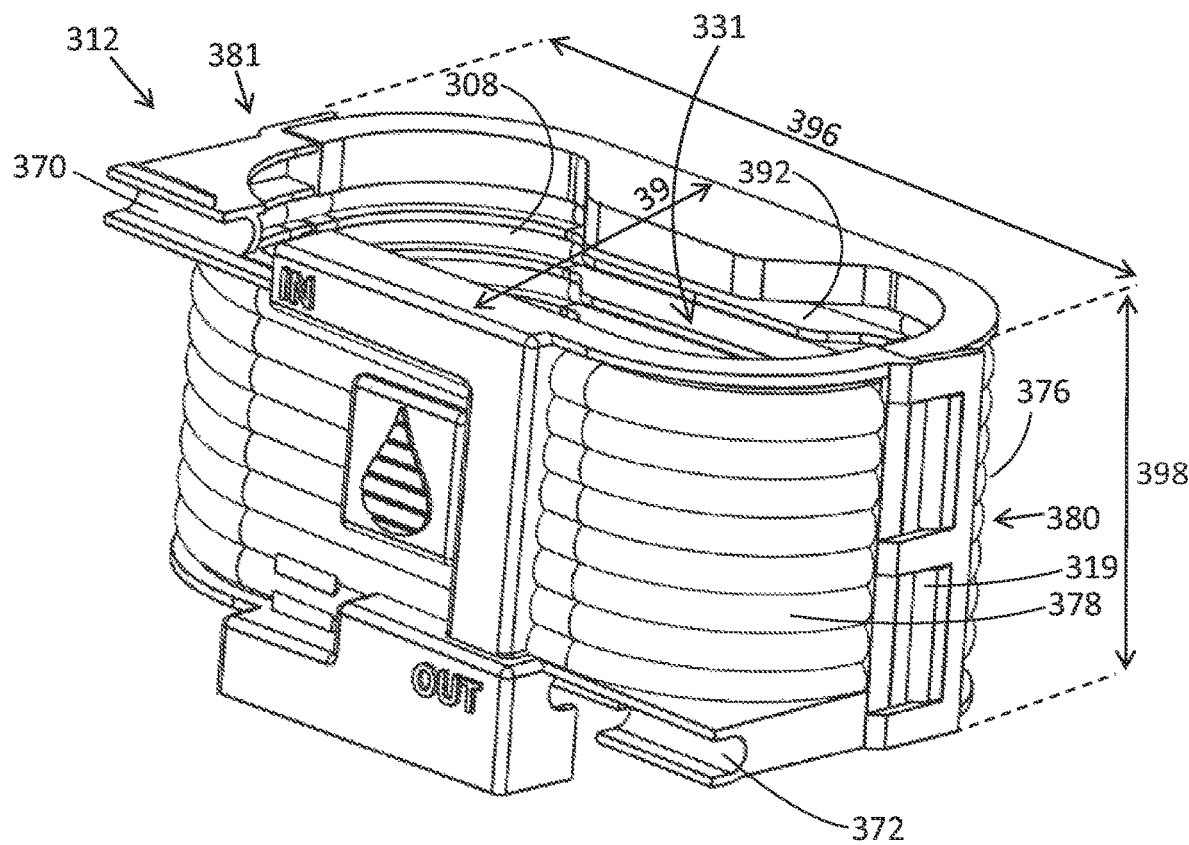
FIG. 3A is a simplified schematic of a first portion of an infusion device, according to some embodiments of the invention.

FIG. 3A is a simplified schematic of a first portion 312 of an infusion device, according to some embodiments of the invention.

Figure 3B:
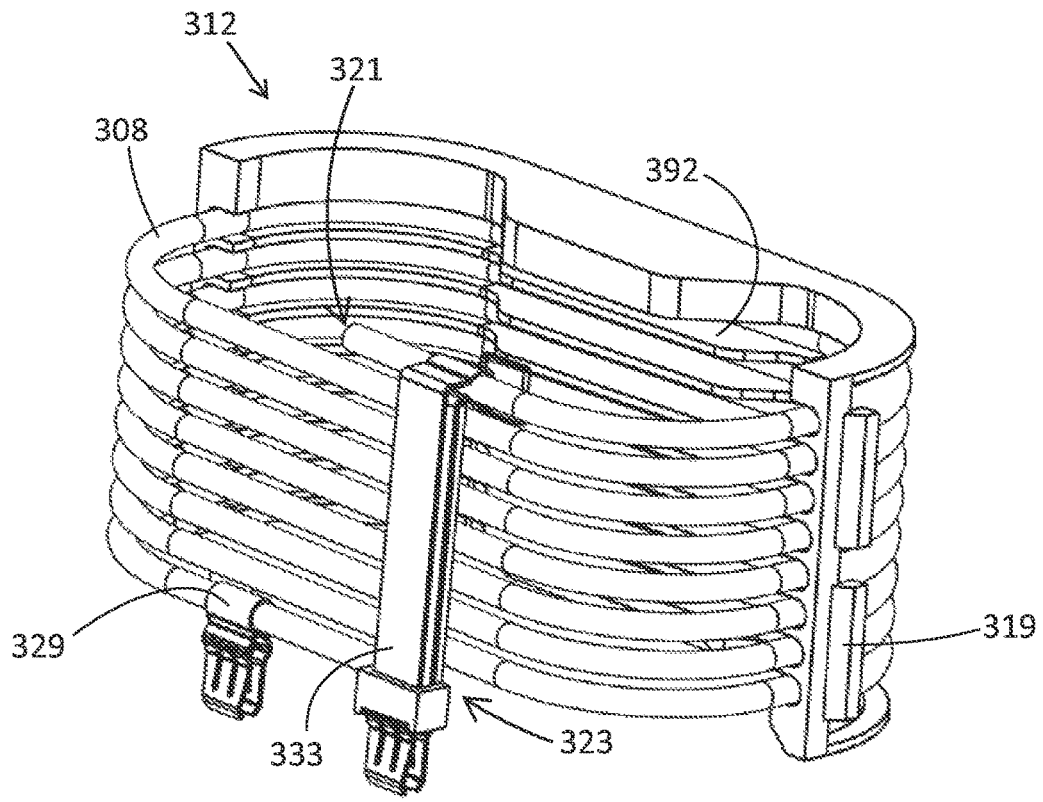
FIG. 3B is a simplified schematic of parts of a first portion of an infusion device, according to some embodiments of the invention.

FIG. 3B is a simplified schematic of parts of a first portion 312 of an infusion device, according to some embodiments of the invention.

In some embodiments, FIG. 3A and FIG. 3B both illustrate the same first portion 312, where, FIG. 3B illustrates first portion 312 where a housing part 378 has been removed.

In some embodiments, first portion 312 (e.g. of FIG. 3A and/or FIG. 3B) includes one or more feature as illustrated and/or described regarding first portion 112 FIG. 1.

In some embodiments, first portion 312 includes a conduit 308 which, in some embodiments, includes one or more feature of conduit 108 FIG. 1.

In some embodiments, conduit 308 includes electrically and/or thermally conductive material. For example, is made of electrically and/or thermally conductive material (for example, metal e.g. stainless steel, aluminum and/or combinations thereof). In an exemplary embodiment, conduit 308 includes (e.g. is formed of) stainless steel. In some embodiments, the conduit 308 includes electrically conductive material (e.g. a conductive coating e.g. an electrically conductive wire) attached to a tubular structure.

In some embodiments, conduit 308 is an elongate structure having a lumen (e.g. is tubing) which has a shape including one or more change in direction. In some embodiments, a shape of conduit 308 delineates an inner space 331 also herein termed a first portion lumen 331.

In some embodiments, conduit 308 is a coil of tubing. In some embodiments, the coil has at least one turn, for example, 1-20 turns, or 5-15 turns, or 8-12 turns, or about 9 turns, or lower or higher or intermediate numbers of turns.

In some embodiments, a total length for conduit 308 is selected based on a desired impedance of conduit 308. In some embodiments, conduit 308 lacks coils. In an exemplary embodiment, coiling of the conduit is defined by a minimum coil size allowed by the material of conduit 308 e.g. a minimum coil size allowed without risk of cracking and/or other mechanical failure of the tube in a manufacturing coiling process. A potential benefit of an increased number of coils (e.g. for a given conduit length) is reduced size of the device. In an exemplary embodiment, conduit 308 is a stainless steel tube coil, where the tube cross section (inner and/or outer cross sectional dimension) is 0.5-10 mm, or 1-5 mm, or 2-4 mm or about 3 mm, or lower or higher or intermediate ranges or diameters. In some embodiments, walls of the conduit are sufficiently thin and/or the conduit material is sufficiently thermally conducting that measurements of the temperature of the conduit sufficiently accurately portray a temperature of the fluid within the conduit. In some embodiments, a thickness of walls of conduit is 0.01-1 mm, or 0.05-1 mm, or 0.1-0.7 mm, or 0.2-0.5 mm, or lower or higher or intermediate ranges or thicknesses. In some embodiments, (for example, for tube cross section of 0.5-10 mm, or 1-5 mm, or 2-4 mm or about 3 mm, or lower or higher or intermediate ranges or diameters) a total length of the conduit e.g. as measured along a central longitudinal axis of the coil is 1000-5000 mm, or 1000-3000 mm, or 2000-3000 mm, or 2100-2300 mm, or about 2200 mm or lower or higher or intermediate lengths or ranges.

In some embodiments, a wider cross section for the conduit is employed. For example, where high fluid supply rate/s are desired (e.g. blood supply during hemorrhage e.g. irrigation). In some embodiments, tube cross section is 2-15 mm, or 3-6 mm, or 4-5 mm, or lower or higher or intermediate cross sections or ranges. Where, for example, for this cross section, in some embodiments, total length of the conduit is 2000-4000 mm, or 2500-3500 mm, or about 3000 mm, or lower or higher or intermediate lengths or ranges.

In some embodiments, first portion 312 includes a housing 376, 378 (including one or more feature of housing 120 FIG. 1).

In some embodiments, housing 376, 378 covers outer portions of conduit 308 while leaving inner portion/s of conduit uncovered. A potential benefit being the ability to position sensor/s of the second portion in close proximity to the conduit potentially increasing accuracy of sensing of the conduit (e.g. conduit temperature).

In some embodiments, housing 376, 378 mechanically supports conduit 308 e.g. coil structure of conduit 308 e.g. additionally or alternatively to covering the coil. For example, in some embodiments, housing 376, 378 includes protrusions 392 which, in some embodiments, protrude inwards from the housing body 376, 378 towards, and optionally, past, the coil into a central region of space defined by the coil structure. Where, in some embodiments, protrusions 392 are aligned with and/or at least partially enter into spaces 317 between turns of the coil of conduit 308. In some embodiments, housing 376, 378 has a protrusion 392 for each space 317 of conduit 308. A potential benefit of protrusions 392 is mechanical strengthening of conduit 308 e.g. potentially reducing risk of shape deformation and/or breakage and/or electrical short-circuiting of conduit 308. In some embodiments, protrusions 392 are electrically and/or thermally insulating. For example, formed of insulating plastic. Electrical insulation potentially preventing short-circuits between turns of conduit 308.

In some embodiments, housing 378 includes one or more support for a connection to a fluid reservoir and/or a connection to an infusion apparatus. For example, in some embodiments, housing In some embodiments housing 378 includes a guide 370 sized and/or shaped to receive tubing and/or other connecting element/s for connection to a fluid reservoir (e.g. the fluid reservoir and/or tubing including one or more feature of fluid reservoir 106 and/or connecting element/s 142, 144 of FIG. 1). In some embodiments housing 378 includes a guide 372 sized and/or shaped to guide connecting element/s for connection to an infusion apparatus (e.g. the connecting element/s including one or more feature of element/s 146, 148 of FIG. 1). In some embodiments, one or both of guides 370, 372 includes a concavity and/or protrusion.

In some embodiments, when housing 378 is in position over conduit 308, guide/s 370, 372 are aligned with conduit openings 321, 323 (e.g. a conduit inlet 321 and a conduit outlet 323 respectively). Where in FIG. 3B conduit outlet 323 is located behind connector 333 and is not directly visible in the figure. For example, so that connective tubing when guiding into housing by the guide/s 370, 372 connects with the associated opening in conduit 308.

In some embodiments, the first portion housing includes more than one housing portion 376, 378 (e.g. two housing portions 376, 378). Where, in some embodiments, the housing portions connect around conduit 308. Where connection between housing portions 376, 378, is, for example, by interlocking of connecting portion/s at one or more connection region 380. In some embodiments, each housing portion 376, 378 includes at least one connector portion (connector portion/s including, in some embodiments, protrusions and recessions) on each side of the housing.

For example, referring to connection region 380, front housing portion 378 includes at least one notch into which a protrusion 319 of back housing portion 376 fits into to connect the portions 376, 378. In an exemplary embodiment e.g. as illustrated in FIGS. 3A-B each housing portion connection region 380, 381 includes two such connections.

In some embodiments, housing 376, 378 includes insulating material e.g. electrically insulating material e.g. thermally insulating material. In some embodiments, housing (optionally, including protrusions 392) is insulating (e.g. electrically and/or thermally insulating). For example, includes and/or is formed of an insulating material e.g. polymer.

In some embodiments, first portion 312 includes one or more electrical connectors 333, 329. For example, in some embodiments, a first electrical connector 333 connected to a beginning region of the coil of conduit 308 and a second electrical connector 329 connected to a final region of the coil. Where, in some embodiments, voltage applied (e.g. through connection of connectors 333, 329 to second portion 414) results in current flowing through conduit 308 which heats the conduit 308.

Figure 9:
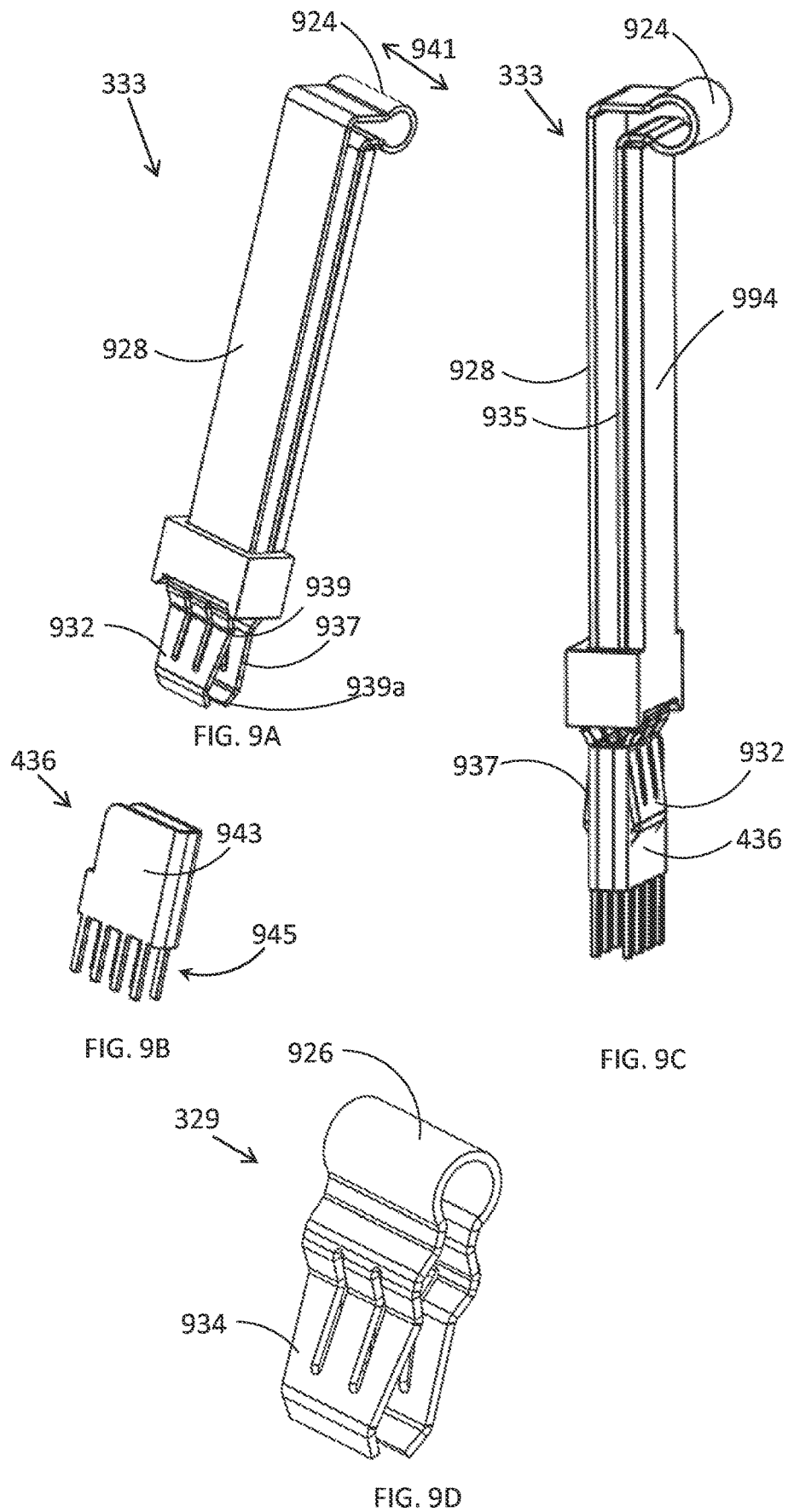
FIG. 9A is a simplified schematic of a connector, according to some embodiments of the invention.
FIG. 9B is a simplified schematic of a contact, according to some embodiments of the invention.
FIG. 9C is a simplified schematic of a connector and a contact, according to some embodiments of the invention.
FIG. 9D is a simplified schematic of a connector, according to some embodiments of the invention.

Additional exemplary details regarding connectors 333, 329 are described regarding FIGS. 9A-C.

FIG. 4A is a simplified schematic of a second portion 414 of an infusion device, according to some embodiments of the invention.

Figure 4B:
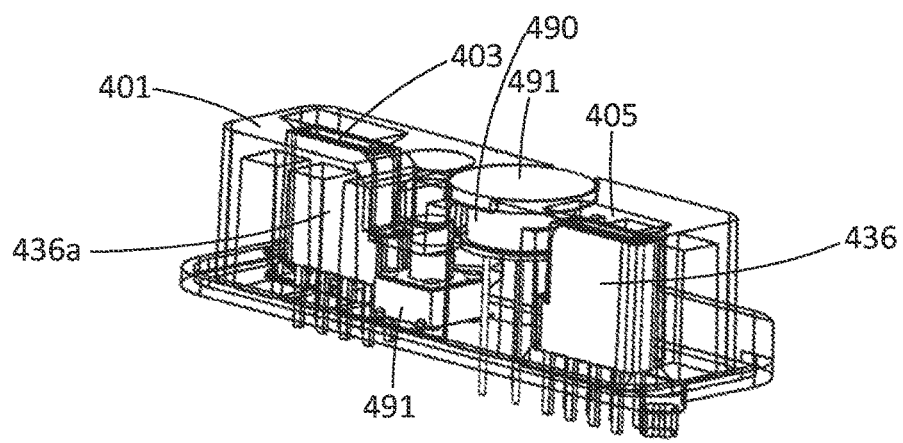
FIG. 4B is a simplified schematic of a part of an infusion device second portion, according to some embodiments of the invention.

FIG. 4B is a simplified schematic of a part of an infusion device second portion 414, according to some embodiments of the invention.

In some embodiments, second portion 414 includes one or more feature as described and/or illustrated regarding second portion 114 FIG. 1.

In some embodiments, second portion 414 includes a housing 422 (e.g. including one or more feature of housing 122 FIG. 1).

In some embodiments, second portion 414 hosts one or more sensor. Where, in some embodiments, one or more sensor senses conduit (e.g. conduit 308 FIGS. 3A-3B) through a window 482, 484, 486, 490 in housing 422. In some embodiments, more than one sensor senses the conduit through a single window. In some embodiments, a sensor senses the conduit through more than one window. In an exemplary embodiment, each sensor senses the conduit through a dedicated window. Where, in some embodiments, the window is adjacent to the conduit. For example, in close contact and/or direct contact with the window e.g. with a separation between the window and the conduit (and/or between the conduit and the sensor) of at most 0.1-2 mm, 0.1-1 mm, or 0.1-0.5 mm, or lower or higher or intermediate ranges or distances.

A potential benefit of window/s e.g. as opposed to holes is sealing of the second portion to entry of dirt and/or dust and/or fluids and/or increased ease of cleaning of the second portion (e.g. for re-use).

Where, in some embodiments, the window/s are transparent to the sensed radiation by the sensor/s. For example, where sensing is of infrared (IR) radiation by IR sensor/s, in some embodiments, the window covering material is transparent to IR (e.g. minimally attenuating e.g. by less than 20%). For example, the material includes one or more of silicon, and germanium, Poly(methyl methacrylate), polycarbonate, Zinc Selenide (ZnSe), Zinc Sulfide (ZnS), Calcium Fluoride (CaF2) and Magnesium Fluoride (MgF2). In an exemplary embodiment, the window/s include and/or are formed of germanium.

In some embodiments, housing 422 includes a base 423 and a body 425. In some embodiments, body 425 is sized and/or shaped to fit into an space delineated by the conduit 308 FIGS. 3A-B. In some embodiments, base 423 forms a step 427 extending away from body 425. In some embodiments, body 425 and step 427 are sized and/or shaped to hold first portion (e.g. first portion 312 FIGS. 3A-B) in position on second portion 414.

In some embodiments, step 427 hosts electrical connection between first and second portions 414, 312. For example, hosts a electrical connection housing 401 which, in some embodiments, is a portion of base 423 which extends away from step towards body 425.

In some embodiments, FIG. 4B illustrates electrical connection housing 401 and contents thereof. Where in FIG. 4B housing 401 is illustrated transparent. In some embodiments, electrical contacts of second portion 414 are housed by electrical connection housing 401, contact openings 403, 405, providing access to the contacts.

In some embodiments, electrical connection housing 401 is a separate unit which is removable and/or replaceable. A potential benefit being potential extension of lifetime of second portion 414 when connections are worn (e.g. associated with the connections being open and potentially exposed to dirt and/or fluid) but other portion/s of second portion 414 remain functional.

Optionally, in some embodiments, second portion 414 includes a switch 491 (e.g. a microswitch) which is engaged when first portion 312 (FIG. 3A and/or FIG. 4B and/or FIG. 5) is attached to second portion 414. In an exemplary embodiment, power supply to first portion 312 is connected only when switch 491 is engaged. A potential advantage being that the device operated only when switch 491 verifies that the portions 414, 312 are aligned correctly e.g. for accurate sensing by the sensor/s of second portion 414. In some embodiments, switch 491 is hosted by electrical connection housing 401.

Optionally, in some embodiments, housing 401 hosts a sensor 490 and/or a window 491 to sensor 490. Where, in some embodiments, sensor 490 is an IR sensor, for example, an analog IR sensor.

Referring back now to FIG. 4A, in some embodiments, second portion 414 includes a connector 466 for connection of the first and second portions 312, 414. In some embodiments, connector 466 is a latch 466 connector. Where, when latch 466 is connecting first and second portion 312, 414, latch 466 extends from a connection 468 to second portion 414 to overlap first portion 312 housing 376.

Optionally, in some embodiments, an opposing end of latch 466, to that overlapping the first portion housing, fits into a notch 480 in second portion 414 housing 425. The double-sided latch connection between the portions, in some embodiments, potentially increasing strength of attachment and/or potentially reducing movement between the portions. Where reduced movement between the portions potentially reduces movement between sensors and the conduit a potential advantage being increased measurement accuracy of measurements acquired by the sensor/s.

In some embodiments, 466 latch is a pivot latch pivoting around a connector 469 allowing connection and disconnection of the portions by rotation of the latch. In some embodiments, notch 480 is provided underneath a protrusion 483 in housing of second portion 414.

In some embodiments, pivoting of latch 466 out from notch 480 and/or away from overlapping with first portion 312 allows connection and/or dis-connection of the portions 312, 414.

In some embodiments, second portion 414 includes a handle 462. In some embodiments, handle 462 is sized and/or shaped (e.g. a lumen of the handle 463) to connect the device to a pole e.g. an infusion pole. In some embodiments, handle 462 includes flexible and/or elastic material, the handle, in some embodiments, being opened by deforming the handle to increase a size of an opening 467 for insertion of a pole, the handle then being returned to its previous position to close opening 467.

A potential advantage of being able to connect the second portion e.g. to a pole is the ability to position the infusion device with respect to the fluid reservoir and/or subject e.g. to control pressure on fluid within the device.

In some embodiments, an inner side 465 of handle is textured, texture potentially reducing likelihood of slipping of the device on a pole to which it is attached. The texture e.g. increasing friction between the pole and the handle. In some embodiments, texture includes protrusions e.g. ridges, where texture protrusions are 0.1-3 mm in height above a surface of a body of handle 462.

In some embodiments, second portion 412 includes cable electrical and/or data connection to one or more external device. In some embodiments, the connection/s (not illustrated) exit second portion housing 423 through a strain relief 474. In some embodiments, strain relief 474 reduces strain on the flexible attachment to housing 423 which is, in some embodiments, rigid.

In some embodiments, housing 422 (e.g. including body 425 and base 423) includes and/or is formed of plastic (e.g. molded plastic). In some embodiments, connection of portions of housing/s are by metal attachments e.g. screws and/or nuts. In an exemplary embodiment, housing 422 includes and/or is formed of reinforced nylon, e.g. glass fiber reinforced nylon.

Figure 5:
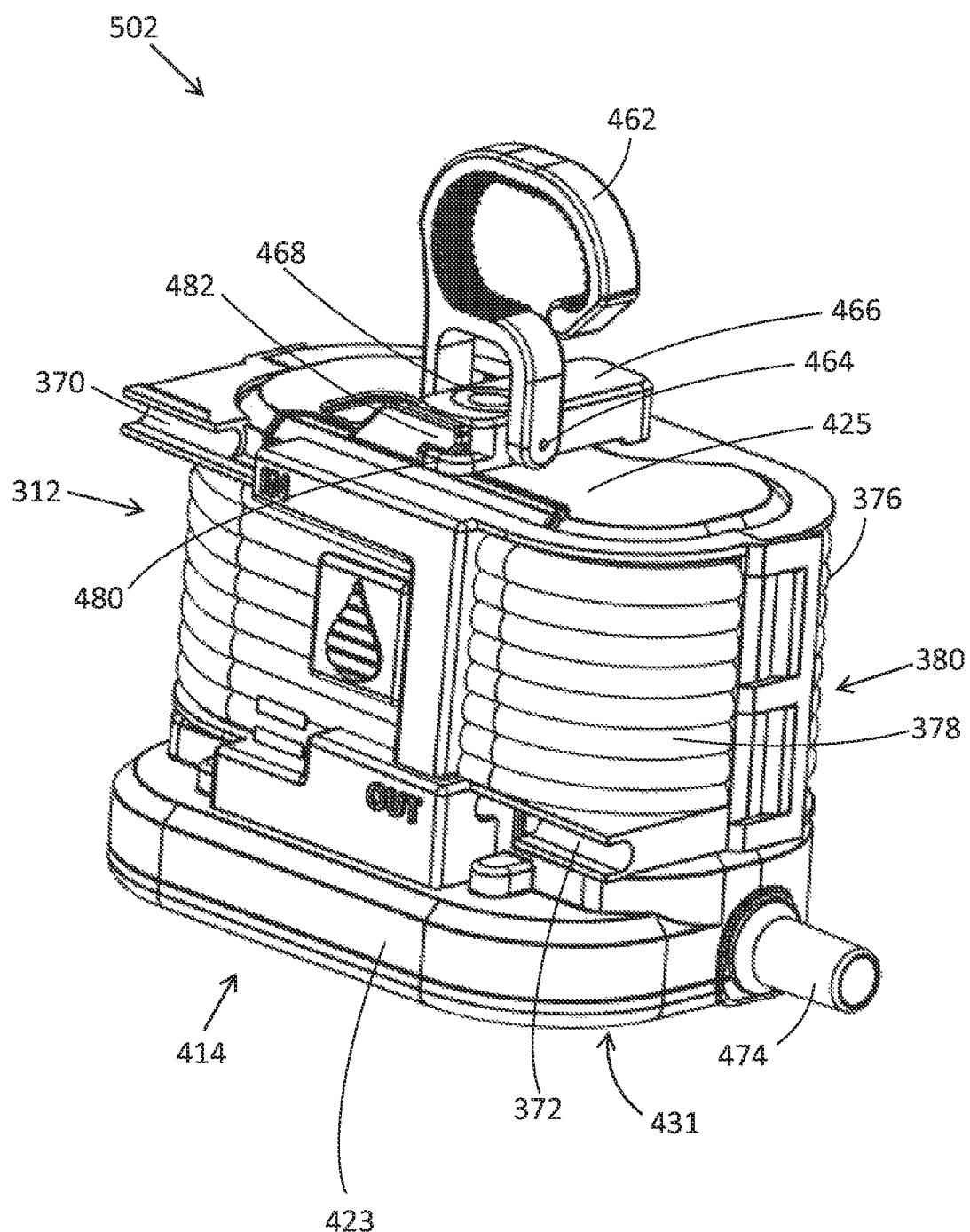
FIG. 5 is a simplified schematic of an infusion device, according to some embodiments of the invention.

FIG. 5 is a simplified schematic of an infusion device 502, according to some embodiments of the invention.

FIG. 5, in some embodiments, illustrates device 502 including first portion 312 and second portion 414 where the portions are coupled.

In some embodiments, first portion 312 includes one or more feature as described regarding and/or illustrated for first portion 312 FIGS. 3A-B and/or first portion 112 FIG. 1. In some embodiments, second portion 414 includes one or more feature as described regarding and/or illustrated for first portion 414 FIG. 4A and/or first portion 114 FIG. 1.

In some embodiments, first portion 312 fits onto second portion 414. Where, in some embodiments, first portion 312 includes a lumen sized and/or shaped to receive body 425 of housing of second portion 414.

For example, as described regarding FIG. 4A, in some embodiments, base 423 of the second portion housing prevents movement of first portion 312 in a body 425 to base 423 direction.

In some embodiments, connector 466 spans an opening to first portion lumen 331, preventing movement of first portion 312 away from second portion 414.

Figure 10:
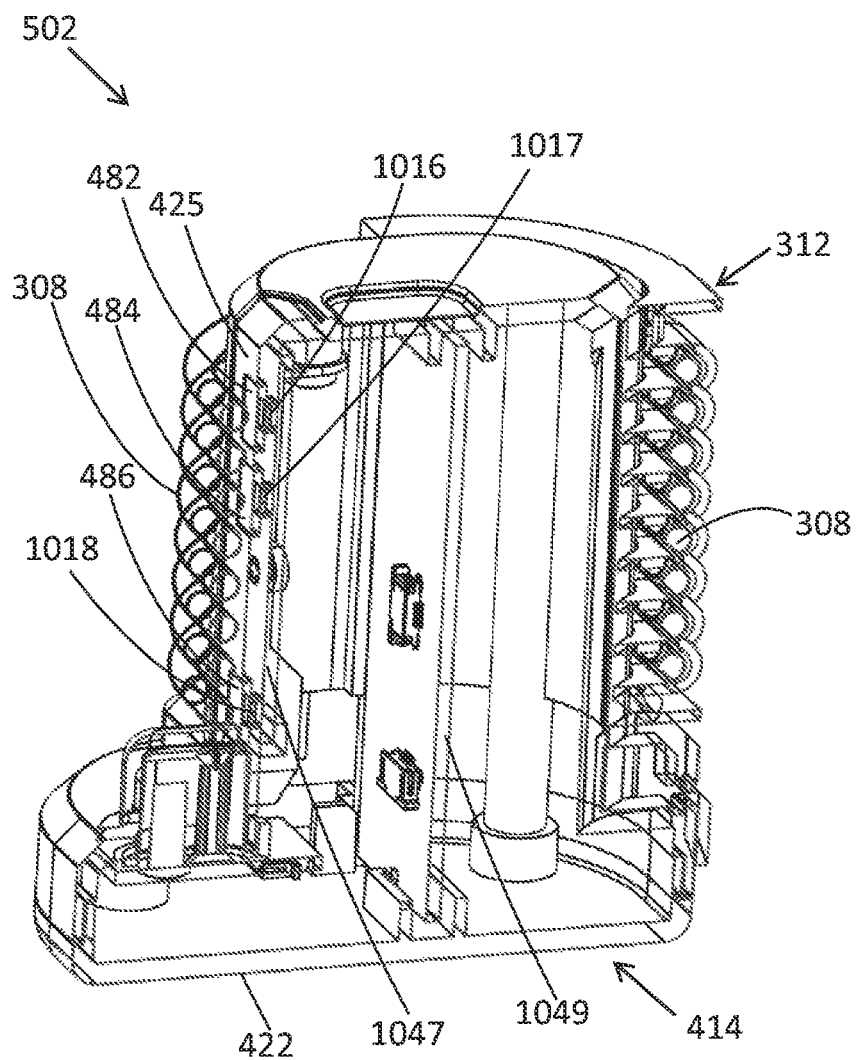
FIG. 10 is a simplified schematic sectional view of an infusion device, according to some embodiments of the invention.

In some embodiments, when first portion 312 is in position with respect to second portion 414 (e.g. as illustrated in FIG. 5), sensors of second portion 414 and/or window/s in second portion (to sensor/s) are aligned with the conduit 308 of first portion 312 e.g. including one or more feature as illustrated in and/or described regarding FIG. 10.

Referring back now to FIG. 3A, in some embodiments, first portion 312 and/or second portion 414 have one or more of a length 396, a depth 387, and a height 398 of 3-20 cm, or 3-15 cm, or 3-10 cm or lower or higher or intermediate numbers or ranges.

Exemplary Methods of Assembly

Figure 6:
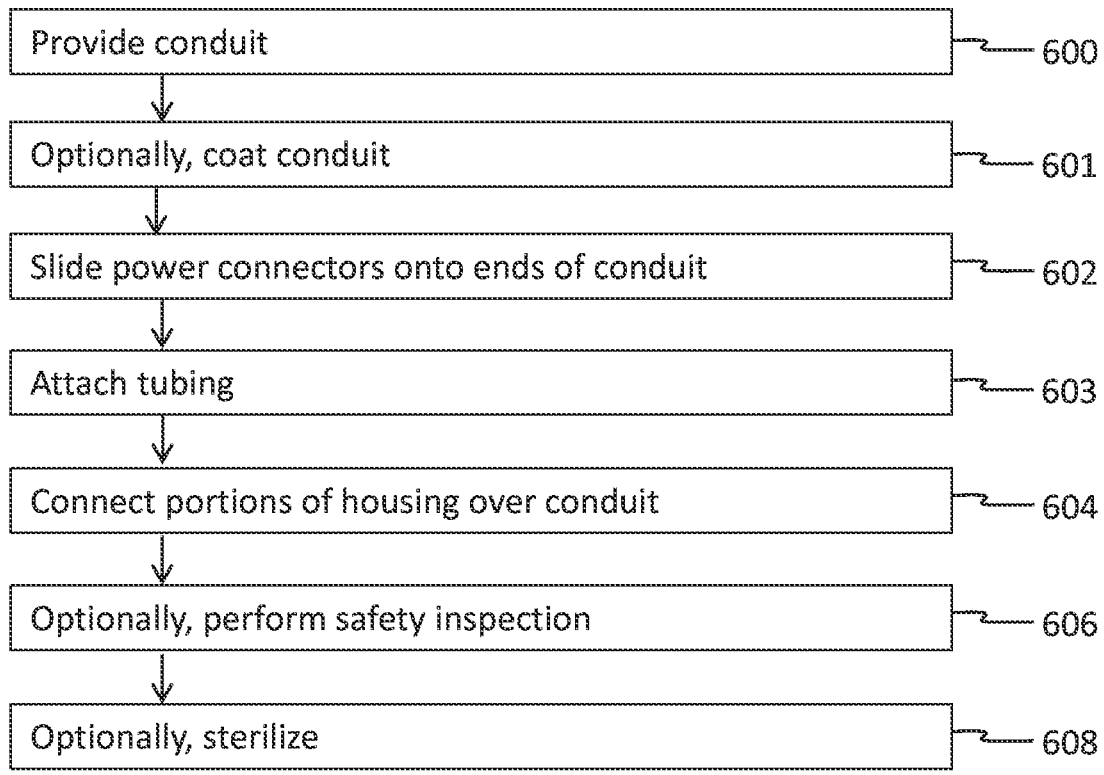
FIG. 6 is a method of assembly of a portion of an infusion device, according to some embodiments of the invention.

FIG. 6 is a method of assembly of a portion of an infusion device, according to some embodiments of the invention.

At 600, in some embodiments, a conduit is provided.

At 601, optionally, in some embodiments, at least a portion of the conduit is coated and/or covered e.g. in IR absorptive material (e.g. as described elsewhere in this document).

At 602, in some embodiments, power connectors are slid onto two ends of the conduit.

At 603, in some embodiments, connective tubing is attached to the conduit.

For example, an tube for connection of a fluid reservoir to the conduit inlet. For example, a tube for connection of an infusion apparatus is connected to the conduit outlet. In some embodiments, the tube connected is PVC tubing, where, in some embodiments, elastic deformation of the tubing seals connection between the tubing and the conduit.

At 604, in some embodiments, portions of a conduit housing are connected over the housing.

At 606, in some embodiments, a safety inspection is performed. For example, including a visual inspection. For example, including a fluid conduit check, where fluid is passed through the conduit to check that fluid flow is suitable e.g. no blockage/s and/or no leaks.

At 608, in some embodiments, one or more portion is sterilized. Alternatively, in some embodiments, at least the conduit is provided sterile and sterility is maintained during assembly.

Figure 7:
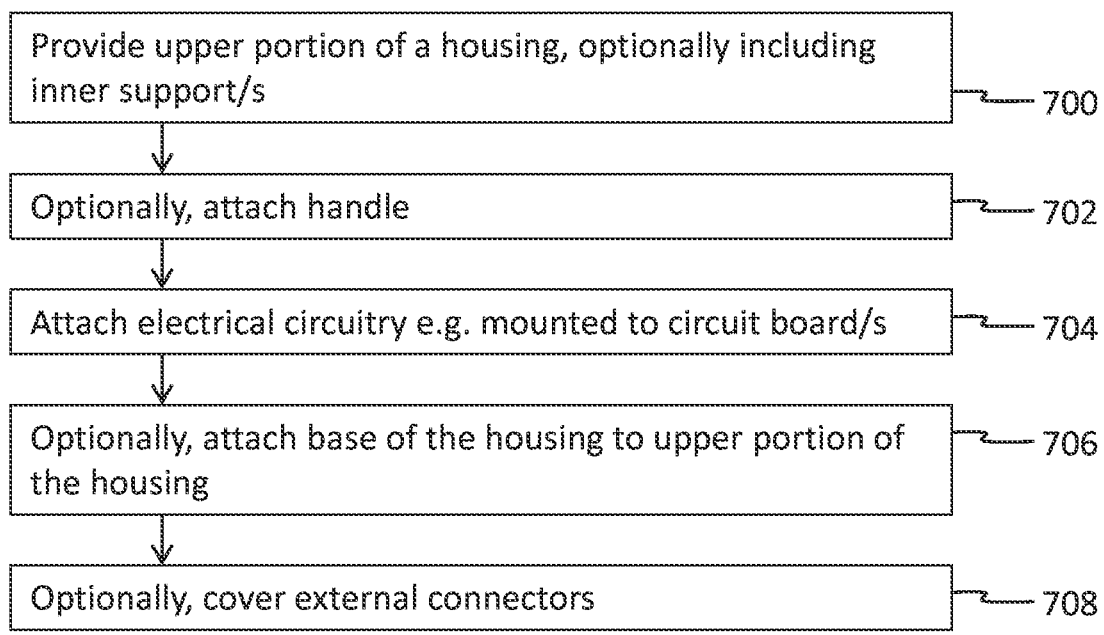
FIG. 7 is a method of assembly of a portion of an infusion device, according to some embodiments of the invention.

FIG. 7 is a method of assembly of a portion of an infusion device, according to some embodiments of the invention.

At 700, in some embodiments, an upper portion of a housing is provided. Where, referring back to FIG. 4A, in some embodiments, the upper portion includes body and base of the housing. Optionally, in some embodiments, the upper portion includes one or more support within the upper portion.

At 702, optionally, in some embodiments, a handle is attached to the upper portion of the housing. For example, by a connector from within the housing extending to the handle disposed externally on the housing. Where, exemplary connectors include, for example, a screw, a screw and a bolt, snap fit portions connecting from either side of the housing.

At 704, in some embodiments, electrical circuitry is attached. For example, by being placed within the housing. In some embodiments, one or more circuit board is positioned within the housing and/or attached to the housing. Where, in some embodiments, supports assist in positioning and/or preventing movement of the circuitry and/or circuit board/s. In some embodiments, element/s are attached to the support/s e.g. by adhesive and/or connecting element/s. In some embodiments, for example, alternatively or additionally to attaching of circuitry and/or circuit boards to the upper portion of the housing, circuitry and/or circuit board/s are attached to a base of the second portion housing (referring back to FIG. 4A, base 431).

At 806, in some embodiments, the base to the second portion housing is attached to the upper portion of housing, for example, closing the housing. Optionally, in some embodiments, prior to closing of the housing (e.g. with the base) a power supply is inserted into the space defined within the housing. Where the power source is electrically connected to circuitry within the housing prior to and/or after insertion of the power source into the housing.

Exemplary Method of Treatment

Figure 8:
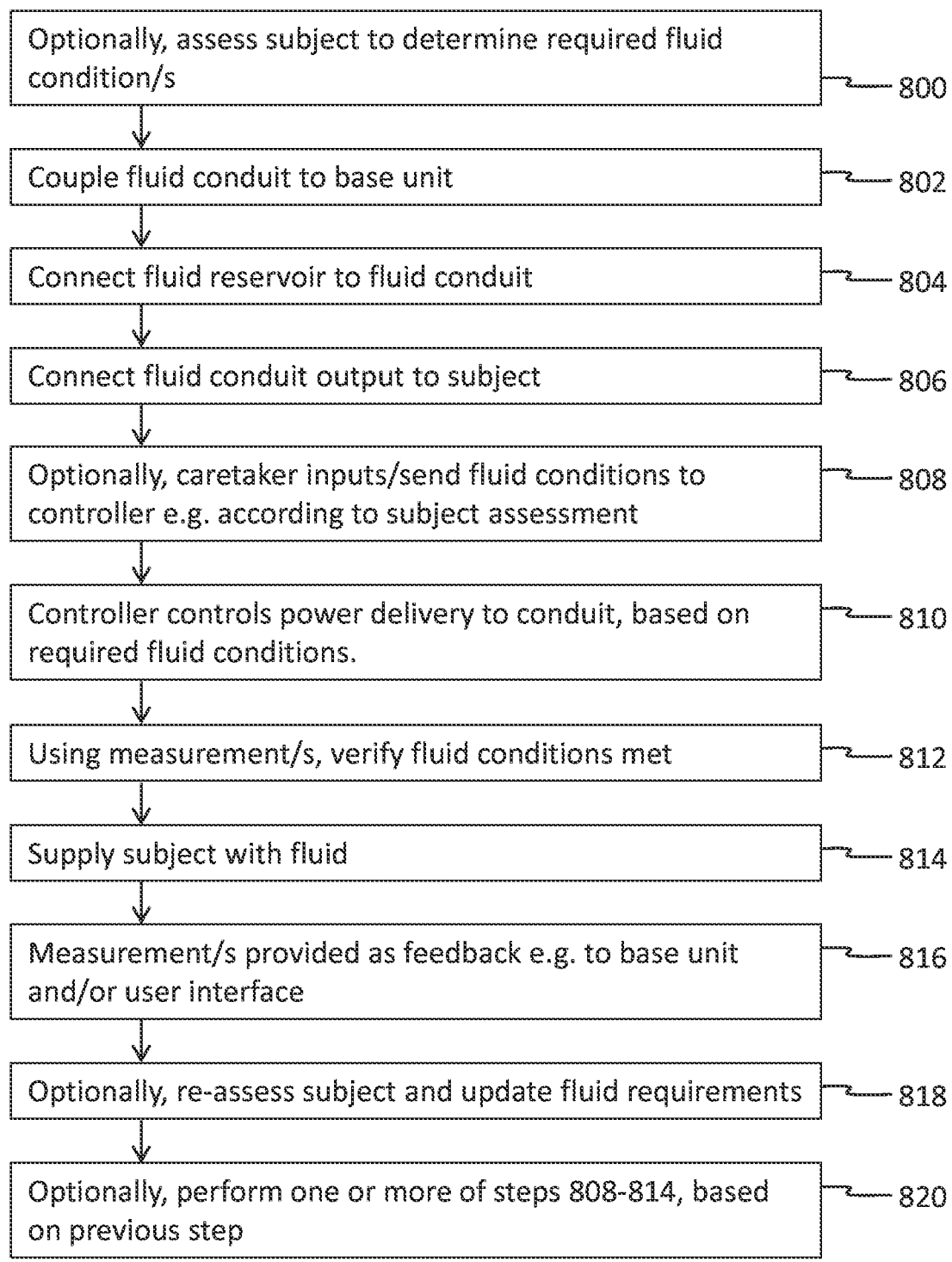
FIG. 8 is a method of treatment using an infusion device, according to some embodiments of the invention.

FIG. 8 is a method of treatment using an infusion device, according to some embodiments of the invention.

At 800, in some embodiments, a subject is assessed. For example, by a medical professional. The assessment, in some embodiments, determining whether the subject requires fluid infusion and/or what condition/s are required of a fluid infusion for the subject.

Where conditions include one or more of, fluid type, fluid flow rate, fluid temperature, location on the patient for infusion, infusion apparatus (e.g. size of infusion tubing)

At 802, in some embodiments, a fluid conduit is coupled to a base unit. For example, where the fluid conduit is provided by a "first portion", for example, as described elsewhere within this document (e.g. first portion 112 FIG. 1, e.g. first portion 312 FIGS. 3A-B and/or FIG. 5). In some embodiments, the base unit includes one or more feature of "second portion/s" as described elsewhere in this document (e.g. second portion 114 FIG. 1, e.g. second portion 414 FIG. 4A and/or FIG. 5).

In some embodiments, the fluid conduit is coupled to the base unit e.g. by being placed on and/or around and/or over a portion of the base unit. In some embodiments, the fluid conduit is connected to the base unit e.g. by one or more connector.

At 804, in some embodiments, a fluid reservoir is fluidly connected to the fluid conduit. For example by attaching a tubing of an infusion bag to an inlet of the fluid conduit. Where, in some embodiments, tubing is flexible and/or elastic, appropriate sizing of the conduit inlet and/or tubing enables a sealed fluid connection.

At 806, in some embodiments, the fluid conduit is fluidly connected to a subject. For example, by attaching an infusion apparatus inlet to the conduit and an infusion apparatus outlet to the subject. Where, in some embodiments, infusion apparatus is flexible and/or elastic, appropriate sizing of the conduit outlet and/or tubing of the infusion apparatus enables a sealed fluid connection.

In some embodiments, one or more of steps 804, 806, 808 are performed in a different order.

At 808, optionally in some embodiments, one or more parameter for fluid conditions is received by the base unit e.g. according to the assessment performed in step 800. For example, inputted to the unit by a user through a user interface (e.g. 154 FIG. 1). For example, received by the unit processor 150 e.g. from a remote processor 152. Alternatively, in some embodiments, fluid conditions are automatic and/or set.

At 810, in some embodiments, a controller (e.g. hosted by the base unit) controls fluid flowing through the conduit according to the fluid condition/s parameter/s. For example, the fluid conduit is heated while fluid flows through the conduit according to required temperature of fluid to be infused.

At 812, optionally in some embodiments, measurements are collected during control of the fluid by the base unit, and, in some embodiments, the measurements are used to verify that fluid conditions have been met.

At 814, in some embodiments, the subject receives infusion fluid, optionally after measurement/s verifying that required fluid parameter/s are fulfilled.

At 816, in some embodiments, fluid is monitored, where measurement/s (e.g. collected by the base unit) are used as feedback e.g. to the base unit and/or user interface. For example, in some embodiments, temperature measurement feedback is used as an input to heating circuitry of the base unit. For example, measurement/s are used as feedback to a user interface e.g. to indicate that a user needs to perform an action e.g. to supply another fluid reservoir.

At 818, optionally, in some embodiments, the subject is re-assessed (e.g. periodically).

At 820, optionally, in some embodiments, the re-assessment is used in one or more of steps 808-814. For example, in some embodiments, the re-assessment is used to update (e.g. change) the fluid condition parameter/s at the base unit e.g. as described regarding step 808.

Exemplary Electrical Connections

FIG. 9A is a simplified schematic of a connector 333, according to some embodiments of the invention.

FIG. 9B is a simplified schematic of a contact 436, according to some embodiments of the invention.

FIG. 9C is a simplified schematic of a connector 333 and a contact 436, according to some embodiments of the invention.

FIG. 9D is a simplified schematic of a connector 329, according to some embodiments of the invention.

In some embodiments, FIG. 9A and FIG. 9C illustrate connector 333 of FIG. 3B, a part of first portion 312, which electrically connects conduit 308 to second portion 414 (FIG. 4A) e.g. to contact 436 of second portion (where, in some embodiments, contact 436 is housed by electrical connection housing 401 FIG. 4A). In some embodiments, FIG. 9D illustrates connector 329 of FIG. 3B, a part of first portion 312, which electrically connects conduit 308 to second portion 414 (FIG. 4A) e.g. to a contact of second portion 414, where, in some embodiments, the contact includes a component as illustrated in FIG. 9B e.g. mounted to a circuit board.

In some embodiments, connector 333 includes a first contact 924 and a second contact 932 connected by a body 928, 935. In some embodiments, first contact 924 electrically contacts a conduit (e.g. conduit), for example, by extending around a portion of the conduit.

In some embodiments, one or both of contacts 924, 926 are configured to be slid onto the conduit (e.g. conduit 308 FIG. 3B and/or FIG. 10). For example, having a lumen sized and/or shaped to receive conduit 308.

In some embodiments, first contact 932 and/or second contact 937 of connector 333 (and/or contact 934 of connector 329) are standard high power contacts which are, in some embodiments, connectable and de-connectable a large number of times e.g. at least 5-1000 times, or at least 20-100 times, or lower or higher or intermediate numbers or ranges. Where contacts 924, 926, 436, are high power as defined as being able to pass power of at least 100 W-2 kW, or 100 W-1 kW, or 600-800 W, or lower or higher or intermediate ranges or powers.

In some embodiments, the connector body includes at least one side which extends from first contact 924 to second contact 932. Optionally, in some embodiments, the connector body includes two sides 928, 935, where each part 928, 935 extends from a different side of first contact 924. Optionally, in some embodiments, second contact 932 includes two contact sides, 932, 937. Where, in some embodiments, each side 932, 937 extends from a side of connector body 928, 935 respectively.

In some embodiments, contact side/s 932, 937 include one or more portion which is deflected (e.g. elastically) when contact sides/s 932, 937 are in position on second portion contact 436 e.g. as illustrated in FIG. 9C. Where, in some embodiments, reactive force of contact side/s 932, 937 onto contact 436 potentially increase quality of electrical connection between the contact/s and/or reduce likelihood of dislodgement and/or disconnection between the first portion contacts 932, 937 and the second portion contact 436.

In some embodiments, a shape of a contact (e.g. both of contacts 932, 937) includes one or more a narrowing 939, 939a where one or both of contacts 932, 937 includes portion/s of the contact which is closer (e.g. veers towards) towards a center of a space defined by connector body portion/s 928, 935 and/or contact side/s 932, 932.

In some embodiments, narrowing/s 939, 939a have a smaller dimension in one or more dimension than second portion contact 436. Where, in some embodiments, connecting the connectors 333, 436 deflects (e.g. elastically) at least portion/s of contact/s 932, 937 at narrowing 939.

In some embodiments, conduit contact/s 924, 926 itself provides both electrical and mechanical connection to the conduit. Where, in some embodiments, contact 924 surrounds the conduit for at least 10-95%, or 30-70%, or 40-60%, or lower or higher or intermediate ranges or percentages of a circumference of the conduit cross section. In some embodiments, for example, as illustrated in FIGS. 3B, 9A, 9C contact 924 extends around a proportion of conduit cross section. In some embodiments, the contact encircles the conduit, at least once. In some embodiments, the contact encircles the conduit, more than once, for example, coiling around the conduit more than one times. In some embodiments, conduit contact/s 924, 926 is wide, having a width 941 of 1-20 mm, or 5-15 mm, or 7-15 mm, or about 8 mm or about 9 mm, or at least 5 mm, or lower or higher or intermediate widths or lengths. In some embodiments, conduit contact/s 924, 926 have a large surface area in contact with the conduit when they are coupled to the conduit. For example, where the surface area in contact is 2PiR x the percentage conduit perimeter contacted by the contact as stated above x exemplary widths stated above, where R is the radius of the conduit, half of exemplary diameters as delineated in the section of this document describing FIG. 3A and/or FIG. 3B.

A potential benefit of contact/s surrounding and/or encircling the conduit and/or being wide being mechanical strength and/or quality of electrical connection between contact 924 and conduit 308 (electrical connection quality e.g. associated with surface area of the contact and conduit in contact with each other).

In some embodiments, conductive material of body 935 is insulated from non-attached portion/s of the conduit. For example, by an insulating separator 994 disposed between body 935 and the conduit. Where, in an exemplary embodiment, separator 994 attaches to connector 333 by fitting around at least a portion of body 928, 935.

Referring now to conduit connector 329 e.g. as illustrated in FIG. 9D and FIG. 3B, in some embodiments, connector 329 includes a first contact 926 and a second contact 934. Where, in some embodiments, first contact 926 includes one or more feature as described and/or illustrated regarding first contact 924 of connector 333.

Where, in some embodiments, second contact 934 includes one or more feature as described and/or illustrated regarding second contact 932, 937. In some embodiments, connector 329 lacks a body and/or separator.

Referring now to second portion contact 436, which, in some embodiments, also illustrates a contact for connection to connector 329. In some embodiments, contact 436 includes a body 943 to which a first portion connector connects. In an exemplary embodiment, contact 436 is attached to a circuit board via pins 945 e.g. for connection to a power supply via the circuit board.

Exemplary Sensing

FIG. 10 is a simplified schematic sectional view of an infusion device 502, according to some embodiments of the invention.

In some embodiments, FIG. 10 illustrates a sectional view of first portion 312 connected to second portion 414 e.g. of the device illustrated in FIG. 5. Where a side 378 (FIG. 3A, FIG. 5) of first portion housing is not illustrated (and/or not present).

Visible in FIG. 10 are windows 482, 484, 486 in second portion housing body 425. In some embodiments, window/s 482, 484, 486 include material more transparent to signal/s measured by sensor/s 1016, 1017, 1018 than other material housing 425. For example, in some embodiments, sensor/s include infrared (IR) sensors 1016, 1017, 1018 for measurement of temperature of conduit 308 (e.g. and, in some embodiments, fluid within conduit). In some embodiments, sensors 1016, 1017, 1018 are aligned each with a respective window. Where, in some embodiments, (e.g. as described regarding FIG. 3A) housing of the first portion holds conduit 308 in position the coils aligned with windows 482, 484, 486 and/or sensors 1016, 1017, 1018. In some embodiments, device 502 includes additional sensor/s, for example, for measurement of other regions of the coil. Sensors, 1016, 1017, 1018, in some embodiments, although sensing different turns of conduit 308, sense a region of the coil. In some embodiments, one or more additional sensor is used to measure other region/s of the coil (e.g. a sensor aligned with window 488 FIG. 4A).

In some embodiments, sensor/s 1016, 1017, 1018 are positioned at, at most, 0.5-5 mm away from window/s 482, 484, 486 respectively. In some embodiments, one or more sensor is in direct contact (e.g. adhered to) a respective window. In some embodiments, sensors 1016, 1017, 1018 are held in position by being mounted to an element 1047 which is, in some embodiments, held in position by second portion housing 422. In some embodiments, element 1047 is a circuit board which provides connection of sensors 1016, 1017, 1018 to other electrical circuitry e.g. to a processor and/or power supply. In some embodiments, additional electrical circuitry of the second portion is mounted to one or more additional circuit board 1049 housed by the second portion housing 422.

Exemplary Safety Feature/s

In some embodiments, the infusion system (e.g. system 100) includes one or more safety feature.

For example, referring back to FIG. 1, in some embodiments, processor, based on received measurements from sensor/s 116, 118, identifies one or more safety risk e.g. temperature outside of a safe range. In some embodiments, upon identifying one or more safety risk, an alert is issued to a user interface and/or power supply to the conduit is disconnected.

In some embodiments, system 100 includes one or more safety feature which is independent of processor 110. A potential benefit being control of circuitry in the case of failure and/or malfunction of processor 110.

In an exemplary embodiment, infusion device 102 includes a cut-off circuit which, in some embodiments, disconnects power supply 110 from conduit. In some embodiments, the cut-off circuit is hosted by second portion 414. In an exemplary embodiment, cut-off circuit is independent of a processor (e.g. processor 150, 152). Where, for example, in some embodiments, the cut-off circuit is configured to act independent of control and/or electrical circuitry e.g. of other part/s of the second portion.

Referring now back to FIG. 4A, second portion 414, in some embodiments, includes a cut-off circuit which includes an analog IR sensor 490. Where, when sensor 490 detects heat over a threshold (e.g. heat of the conduit and/or other circuitry), sensor 490 disconnects the power supply to second portion 414 and/or from second portion 414 to first portion 312. In some embodiments, sensor 490 and sensor 1018 sense conduit 308 (optionally, a same portion of conduit 308), for example, each through an associated window 491 in housing 422 of second portion 414. Where, in some embodiments, windows 422, 491 are adjacent to and/or allow sensing of the conduit from different directions e.g. around a circumference of the conduit. A potential advantage being the ability to calibrate and/or verify measurement from one sensor 490, 1018 using measurement/s from the other of sensors, 490, 1018. In some embodiments, sensor measurements taken from different regions of the conduit are used to self-calibrate the sensors e.g. where assumptions are made about temperature at different points on the conduit (e.g. that the temperature is constant).

In some embodiments, calibration of sensor measurements and/or verification that a sensor is operational is performed (e.g. by a processor e.g. processor 150 and/or 152 FIG. 1) by comparing measurements provided by different sensors.

Exemplary Connector

Figure 11A:
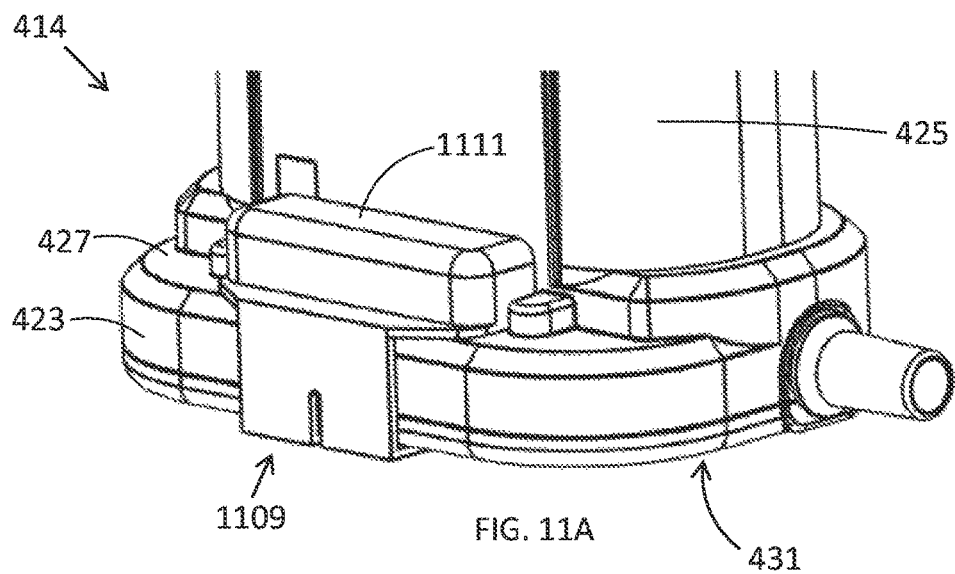
FIG. 11A is a simplified schematic view of a portion of a second portion of an infusion device, according to some embodiments of the invention.

FIG. 11A is a simplified schematic view of a portion of a second portion 414 of an infusion device, according to some embodiments of the invention.

Figure 11B:
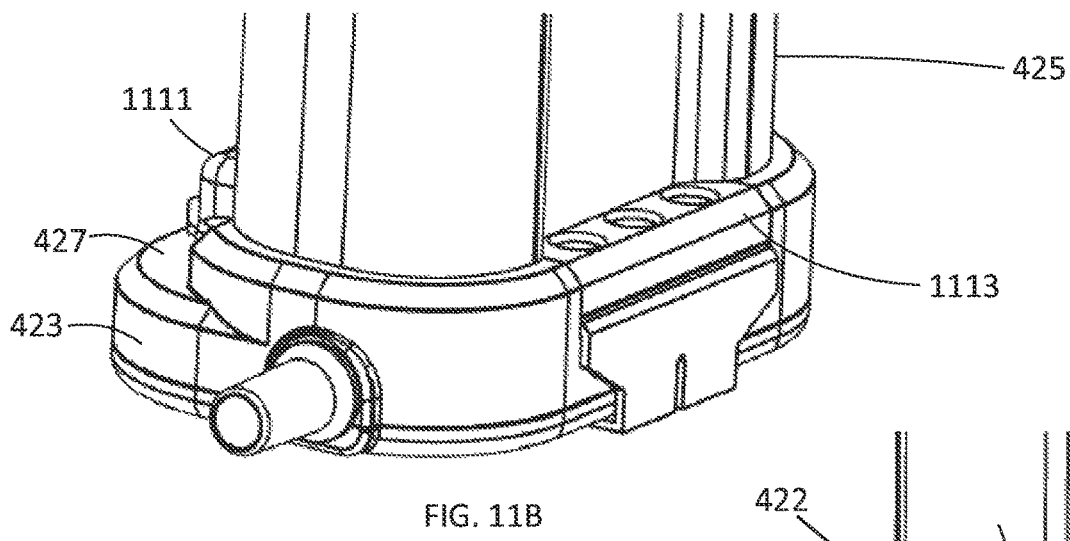
FIG. 11B is a simplified schematic view of a portion of a second portion of an infusion device, according to some embodiments of the invention.

FIG. 11B is a simplified schematic view of a portion of a second portion 414 of an infusion device, according to some embodiments of the invention.

Figure 11D:
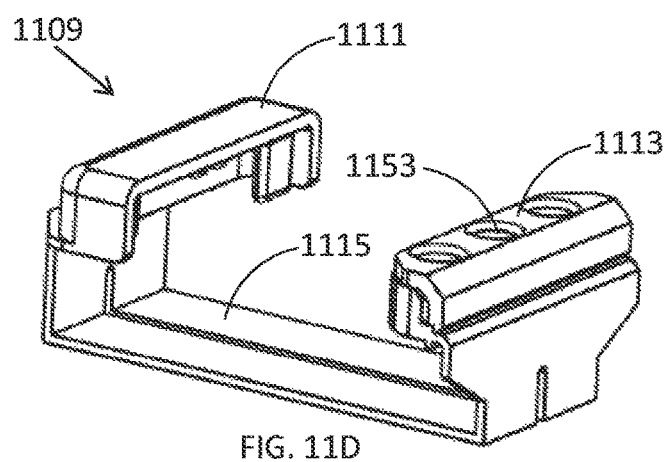
FIG. 11D is a simplified schematic view of a connector, according to some embodiments of the invention.
Figure 11C:
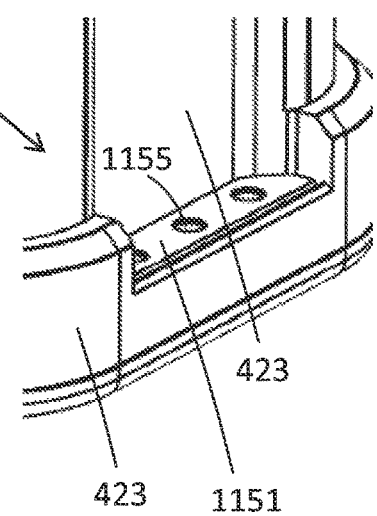
FIG. 11C is a simplified schematic view of a portion of a second portion of an infusion device, according to some embodiments of the invention.

FIG. 11C is a simplified schematic view of a portion of a second portion 414 of an infusion device, according to some embodiments of the invention.

FIG. 11D is a simplified schematic view of a cover element 1109, according to some embodiments of the invention.

In some embodiments, an infusion device system includes a cover 1111 for one or more portion of the device. In some embodiments, covers contact opening/s (e.g. contact openings 403, 405 FIG. 4A) of second portion 414. A potential advantage being protection to the contact/s e.g. from entry of dirt and/or moisture. In some embodiments, cover 1111 surrounds contact opening housing 401 (FIG. 4A), on one or more side, extending, in some embodiments, to housing step 427 (FIG. 4A).

In some embodiments, cover 1109 is part of a base connector 1109 where cover 1111 is disposed on a first side of base connector 1109. Cover element 1109, in some embodiments, including a base 1115 connecting, in some embodiments, cover 1111 to a housing connector 1113. In some embodiments, base connector 1115 is used as handle, for example, for connecting second portion 414 e.g. to a pole or hook In some embodiments, base connector 1109 includes flexible and/or elastic material. In an exemplary embodiment, cover element 1109 includes silicone rubber. For example, in some embodiments, cover 1111 attaches to the contact housing by elastic deformation of the cover material. In some embodiments, elasticity and/or flexibility of base 1115 enables the base to deform around another element (e.g. pole between the base and housing underside 431) e.g. to hold the infusion device onto the element.

In some embodiments, housing connector 1113 extends upwards from underside 431 and, in some embodiments, onto a recession 1151 in second portion 414 housing 422. In some embodiments, connector 1113 is attached to housing 422 by insertion of one or more connector (e.g. screw) into channels 1153 in housing e.g. passing through channels 1153 and extending into aligned channels 1155 in housing 422 e.g. channels 1155 in recession 1151.

In some embodiments, attachment of housing connector 1113 to the housing reduces likelihood of dislodgement of cover 1111 and/or loss of the cover element 1109.

Additional Exemplary Embodiments

FIG. 12A is a simplified schematic of an infusion device 1202, according to some embodiments of the invention.

FIG. 12B is a simplified schematic of an infusion device 1202, according to some embodiments of the invention.

FIG. 12C is a simplified schematic of an second portion 1214 of an infusion device, according to some embodiments of the invention.

In some embodiments, FIGS. 12A-C illustrate the same infusion device 1202.

In some embodiments, first portion 1212 and/or second portion 1214 include one or more feature as described and/or illustrated regarding first portion 112 and/or second portion 114 of FIG. 1 respectively.

In some embodiments, first portion 1212 and second portion 1214 are coupled by placing first portion 1212 is inserted into a lumen 1251 of a housing 1222 of second portion.

In some embodiments, for example, as opposed to e.g. as illustrated in FIGS. 3A-B, FIGS. 4A-B and/or FIG. 5, to sensing being hosted by a portion located within a lumen defined by a conduit coil, sensors are positioned externally to the conduit coil e.g. on one side of the conduit coil. For example, FIG. 12C illustrates windows 1282, 1284 to sensors housed within second portion housing 1222. Where, in some embodiments, windows 1282, 1284 include one or more feature of windows 482, 484, 486, 491 FIGS. 4A-B and/or FIG. 10.

In some embodiments, housing 1222 hosts a switch (e.g. including feature/s of switch 491 FIGS. 4A-B) and/or contact/s (e.g. including feature/s of contacts 436, 436a FIGS. 4A-B and/or FIGS. 9B-C) and/or a sensor (e.g. including feature/s of sensor 490 FIG. 4B).

In some embodiments, lumen 1251 is closed by a cover portion 1253 of housing 1222. Where, in an exemplary embodiments, cover portion 1253 is attached by hinges 1255 to housing 1222.

FIGS. 12B-C, in some embodiments, illustrate device 1202 without cover portion 1253. In some embodiments, however, cover portion opens, e.g. rotating about hinges 1255, e.g. for insertion of first portion 1212.

In some embodiments, second portion 1214 includes a connector 1266 which holds cover portion 1253 in position, for example, thereby holding first portion 1212 in position within lumen. A potential benefit being aligning of the conduit of first portion 1212 with sensors of the second portion.

Optionally, in some embodiments, device 1202 includes a clip 1263 e.g. for attachment of device 1202 e.g. to a pole e.g. IV pole. In some embodiments, clip 1263 is attached to housing 1222 of second portion 1214.

In some embodiments, device 1202 includes connectivity to external power and/or data e.g. through a cable 1275. In some embodiments, cable 1275 extends through a strain relief 1274 (which, in some embodiments, includes one or more feature of strain relief 474 FIG. 4A).

In some embodiments, first portion 1212 includes a handle 1271 in a housing 1276 of first portion 1212. Where, in some embodiments, a user grasps handle 1271 to insert first portion into lumen 1251 e.g. to engage first portion 1212 with second portion 1214 e.g. contacts and/or microswitch.

General

It is expected that during the life of a patent maturing from this application many relevant infusion technologies will be developed and the scope of the terms "infusion", "infusion device" are intended to include all such new technologies a priori.

As used herein the term "about" refers to ±20%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A device for preparation of infusion fluid comprising:
    a first portion comprising:
        a fluid conduit comprising electrically conductive material; and
        electrical circuitry electrically connected to said fluid conduit;
    a second portion configured to be selectively couplable to and detachable from the first portion and comprising:
        at least one sensor for sensing one or both of a parameter of fluid within said fluid conduit and a parameter of said fluid conduit; and
        a power source including one or both of a power supply and connectivity to the power supply or an external power supply;
    wherein mechanical coupling of said first portion to said second portion electrically connects said electrical circuitry to said power source,
    wherein said fluid conduit is elongated, having a shape including one or more change in direction and following a path around an internal volume,
    wherein said fluid conduit is a coil of tubing, said fluid conduit coiling around said internal volume, and
    wherein said second portion includes a body sized and shaped to fit into said internal volume and wherein said mechanical coupling comprises inserting said body into said internal volume and wherein said body shape and a shape of said internal volume are matched so that said mechanical coupling causes said electrical connecting and aligns at least one of said at least one sensor with said fluid conduit.

2. The device according to claim 1, wherein said body fits into said internal volume through an opening to said internal volume and wherein said second portion includes a base portion larger than said opening.

3. The device according to claim 1, wherein said first portion is sized and shaped to fit into a lumen of said second portion.

4. The device according to claim 1, wherein said second portion comprises at least one second portion electrical contact; wherein said electrical circuitry of said first portion comprises at least one first portion electrical contact where, when the first and second portions are mechanically coupled, said at least one second portion electrical contact contacts said at least one first portion electrical contact.

5. The device according to claim 4, wherein said first portion comprises at least one electrical connector electrically connecting said fluid conduit to said at least one first portion electrical contact.

6. The device according to claim 5, wherein at least one of said at least one electrical connector comprises a portion configured to be slid onto said fluid conduit.

7. The device according to claim 6, wherein said portion of said at least one electrical connector is an electrical contact between said at least one electrical connector and said fluid conduit.

8. The device according to claim 7, wherein said portion of said at least one electrical connector comprises a lumen sized and shaped to receive said fluid conduit and form electrical contact with said fluid conduit.

9. The device according to claim 8, wherein said portion of said at least one electrical connector is a loop which extending around at least 50% of a circumference of said fluid conduit.

10. The device according to claim 1, wherein said at least one sensor comprises a non-contact sensor.

11. The device according to claim 10, wherein said non-contact sensor is an infrared (IR) sensor.

12. The device according to claim 1, wherein said second portion comprises a housing, wherein said at least one sensor includes a sensor disposed within said housing of said second portion, wherein upon mechanically coupling of said first portion to said second portion, said sensor disposed within said housing of said second portion is positioned adjacent to a portion of said fluid conduit.

13. The device according to claim 12, wherein said housing of said second portion encloses circuitry of said second portion.

14. The device according to claim 12, wherein said at least one sensor includes a sensor which senses said fluid conduit through a window in said housing of said second portion.

15. The device according to claim 14, wherein said window comprises material transparent to IR radiation.

16. The device according to claim 15, wherein said window comprises germanium.

17. The device according to claim 1, wherein said at least one sensor comprises a contact sensor, where said contact sensor makes contact with said fluid conduit for sensing said fluid conduit upon mechanical coupling of said first portion and said second portion.

18. The device according to claim 1, wherein said electrical power supplied by said power source to said fluid conduit through said electrical circuitry acts to heat said fluid conduit.

19. The device according to claim 1, comprising a processor configured to:
    receive a measurement signal from said at least one sensor, said measurement signal indicating temperature of said fluid; and
    generate control signals to control said power source, based on said measurement signal to control a temperature of said fluid during flow thereof by modifying a heating provided by said fluid conduit.

20. The device according to claim 1, wherein said second portion comprises at least one electrical contact housed in a removable portion of said second portion.

21. The device according to claim 1, comprising a microswitch activated by mechanical coupling of said first portion and said second portion.

22. The device according to claim 21, wherein activating of said microswitch enables power transfer from said power source to said electrical circuitry.

23. The device according to claim 1, wherein one or more portion of said fluid conduit is covered with an infrared absorptive material.

24. The device according to claim 1, wherein said power source is the connectivity to the external power supply, wherein said external power supply is external to said device and is connected to said second portion via connection electrical circuitry.

25. A device for preparation of infusion fluid comprising:
a first portion comprising:
   a fluid conduit comprising electrically conductive material; and
   electrical circuitry electrically connected to said fluid conduit;
a second portion configured to be selectively couplable to and detachable from the first portion and comprising:
   at least one sensor for sensing one or both of a parameter of fluid within said fluid conduit and a parameter of said fluid conduit; and
   a power source including one or both of a power supply and connectivity to the power supply or an external power supply;
wherein mechanical coupling of said first portion to said second portion electrically connects said electrical circuitry to said power source,
wherein said first portion is sized and shaped to fit into a lumen of said second portion,
wherein said fluid conduit is elongated, having a shape including one or more change in direction and following a path around an internal volume, and wherein said fluid conduit is a coil of tubing, said fluid conduit coiling around said internal volume, and
wherein said lumen of said second portion lumen comprises a cover, which is closed to hold said first portion in position within said lumen of said second portion lumen.

26. A device for preparation of infusion fluid comprising:
a first portion comprising:
   a fluid conduit comprising electrically conductive material; and
   electrical circuitry electrically connected to said fluid conduit;
a second portion configured to be selectively couplable to and detachable from the first portion and comprising:
   at least one sensor for sensing one or both of a parameter of fluid within said fluid conduit and a parameter of said fluid conduit; and
   a power source including one or both of a power supply and connectivity to the power supply or an external power supply;
wherein mechanical coupling of said first portion to said second portion electrically connects said electrical circuitry to said power source, and
wherein said first portion comprises a housing which extends around said fluid conduit while having one or more openings to the fluid conduit, where, when said first portion and said second portion are mechanically coupled, at least one of said at least one sensor is adjacent to said one or more openings.

27. A device for preparation of infusion fluid comprising:
a first portion comprising:
   a fluid conduit comprising electrically conductive material; and
   electrical circuitry electrically connected to said fluid conduit;
a second portion configured to be selectively couplable to and detachable from the first portion and comprising:
   at least one sensor for sensing one or both of a parameter of fluid within said fluid conduit and a parameter of said fluid conduit; and
   a power source including one or both of a power supply and connectivity to the power supply or an external power supply;
wherein mechanical coupling of said first portion to said second portion electrically connects said electrical circuitry to said power source,
wherein said device comprises a microswitch activated by mechanical coupling of said first portion and said second portion, wherein activating of said microswitch enables power transfer from said power source to said electrical circuitry, and
wherein said microswitch is housed within a removable portion of said second portion with electrical contacts of said second portion.

* * * * *